United States Patent [19]
Sackler et al.

[11] Patent Number: 5,478,577
[45] Date of Patent: Dec. 26, 1995

[54] METHOD OF TREATING PAIN BY ADMINISTERING 24 HOUR ORAL OPIOID FORMULATIONS EXHIBITING RAPID RATE OF INITIAL RISE OF PLASMA DRUG LEVEL

[75] Inventors: Richard Sackler, Greenwich; Paul Goldenheim, Wilton; Robert Kaiko, Weston, all of Conn.

[73] Assignee: Euroceltique, S.A., Luxembourg

[21] Appl. No.: 156,468

[22] Filed: Nov. 23, 1993

[51] Int. Cl.$^6$ .................................... A61K 9/14
[52] U.S. Cl. .................. 424/489; 424/490; 424/468; 424/457; 424/451; 424/456
[58] Field of Search ................ 424/489, 490, 424/468, 451, 456; 514/356

[56] References Cited

U.S. PATENT DOCUMENTS

| | | | |
|---|---|---|---|
| 4,797,410 | 1/1989 | El Fakahany | 514/356 |
| 5,321,012 | 6/1994 | Mayer et al. | 514/216 |
| 5,330,766 | 7/1994 | Morella et al. | 424/490 |

OTHER PUBLICATIONS

Advertisement: Roxanol SR, ©1988 Roxane Laboratories, Inc.

R. Kaiko and T. Hunt, "Comparison of the Pharmacokinetic Profiles of Two Oral Controlled–Release Morphine Formulations in Healthy Young Adults", Clin. Thera., vol. 13, No. 4, 1991.

R. West and C. Maccarrone, "Single Dose Pharmacokinetics of a New Oral Sustained–Release Morphine Formulation, Kapanol® Capsules", Abstracts—7th World Congress on Pain, Aug. 26, 1993, Abstracts 997–1001.

S. Bloomfield, et al., "Analgesic efficacy and potency of two oral controlled–release morphine preparations", Clin. Pharmacol. Ther., vol. 53, No. 4, pp. 469–478, ©1993.

Advertisement: MS Contin®, ©1986, 1987, The Purdue Frederick Company.

*Primary Examiner*—Thurman K. Page
*Assistant Examiner*—William E. Benston, Jr.
*Attorney, Agent, or Firm*—Steinberg, Raskin, & Davidson

[57] ABSTRACT

Patients are treated with 24-hour oral sustained release opioid formulations which upon administration quickly release an effective portion of the opioid contained therein such that there is an initially more rapid opioid release so that the minimum effective analgesic concentration of the opioid can be more quickly achieved. In the method, the formulations are designed to provide a relatively large peak to trough concentration of the opioid, rather than a flattened serum concentration curve.

10 Claims, 14 Drawing Sheets

METHOD OF TREATING PAIN BY ADMINISTERING 24 HOUR ORAL OPIOID FORMULATIONS EXHIBITING RAPID RATE OF INITIAL RISE OF PLASMA DRUG LEVEL

BACKGROUND OF THE INVENTION

The present invention relates to bioavailable sustained-release pharmaceutical formulations of analgesic drugs, in particular opioid analgesics, which provide an extended duration of effect when orally administered.

It is known in the pharmaceutical art to prepare compositions which provide for controlled (slow) release of pharmacologically active substances contained in the compositions after oral administration to humans and animals. Such slow release compositions are used to delay absorption of a medicament until it has reached certain portions of the alimentary tract. Such sustained-release of a medicament in the alimentary tract further maintains a desired concentration of said medicament in the blood stream for a longer duration than would occur if conventional rapid release dosage forms are administered.

It is the intent of all sustained-release preparations to provide a longer period of pharmacologic response after the administration of the drug and is ordinarily experienced after the administration of the rapid release dosage forms. Such longer periods of response provide for many inherent therapeutic benefits that are not achieved with corresponding short acting, immediate release preparations. This is especially true in the treatment of cancer patients or other patients in need of treatment for the alleviation of moderate to severe pain, where blood levels of an opioid analgesic medicament must be maintained at a therapeutically effective level to provide pain relief. Unless conventional rapid acting drug therapy is carefully administered at frequent intervals to maintain effective steady state blood levels of the drug, peaks and valleys in the blood level of the active drug occur because of the rapid absorption, systemic excretion of the compound and through metabolic inactivation, thereby producing special problems in maintenance of analgesic efficacy.

The prior art teaching of the preparation and use of compositions providing the sustained-release of an active compound from a carrier is basically concerned with the release of the active substance into the physiologic fluid of the alimentary tract. However, it is generally recognized that the mere presence of an active substance in the gastrointestinal fluids does not, by itself, insure bioavailability.

In order to be absorbed, the active drug substance must be in solution. The time required for a given proportion of an active substance from a unit dosage form is determined as the proportion of the amount of active drug substance released from a unit dosage form over a specified time base by a test method conducted under standardized conditions. The physiologic fluids of the gastrointestinal tract are the media for determining dissolution time. The present state of the art recognizes many satisfactory test procedures to measure dissolution time for pharmaceutical compositions, and these test procedures are described in official compendia world wide.

Once-a-day orally administrable dosage forms have previously been developed in the art and are commercially available. However, currently, there are no orally administered opioid formulations commercially available which provide an extended duration of effect, e.g., greater than about 12 hours.

There is a need in the art to develop drug formulations which provide a duration of effect lasting longer than twelve hours such as a drug that may be administered to a patient only once a day. Many of the oral opioid analgesic formulations that are currently available in the market must be administered every four to six hours daily with a selected few formulated for less frequent 12 hour dosing.

Morphine, which is considered to be the prototypic opioid analgesic, has been formulated into 12 hour controlled-release formulations (i.e., MS Contin® tablets, commercially available from Purdue Frederick Company).

It has now been accepted by certain practitioners in the medical and scientific communities that those controlled-release opioids with release characteristics most closely resembling zero order, rather than first order, processes are most desirable. This zero order release provides very slow opioid absorption and minimal peak to trough fluctuation in opioid levels with repeated dosing. Evidence for this has come primarily, if not exclusively, from "Q12H" (12 hourly) comparisons of a sustained-release morphine formulations such as Kapanol® (a product of F.H. Falding and Company) with other morphine formulations (immediate release and sustained release.

For example, a study by west et al., entitled, *Single Dose Pharmacokinetics of a New Oral Sustained-Release Morphine Formulation, Kapanol Capsules,* compared Kapanol with another Q12H controlled-release morphine formulation, MST Continus® and concluded that "Kapanol has a slower absorption rate and a longer duration above 75% peak concentration than MST Continus" and that the "pharmacokinetics of Kapanol are consistent with a sustained release formulation, suitable for at least 12 hourly dosing administration. The slow, sustained absorption of morphine from Kapanol may provide clinical advantages over morphine preparations."

A study by Gourlay et al., entitled, *A Comparison of Kapanol (a New Sustained-Release Morphine Formulation), MST Continus in Morphine Solution in Cancer Patients: Pharmacokinetic Aspects,* provided for pharmacokinetic comparisons at steady state, following Q12H administrations of Kapanol and MST Continus and concluded that "Kapanol has a longer T-max, lower C-max, lower fluctuations in morphine concentrations, and a greater time that morphine concentration exceeds 0.75 C-max, compared to either MST Continus or immediate-release morphine solution. These findings indicate that Kapanol has a superior sustained-release morphine profile than does MST Continus."

A study by Plummer et al., entitled, *A Comparison of Kapanol (a New Sustained-Release Morphine Formulation), MST Continus and Morphine Solution in Cancer Patients: Pharmacodynamic Aspects,* compared the efficacy and side effects of the formulations with the controlled-release products administered every 12 hours, and the immediate-release product every 4 hours. It was concluded that, while there were "no differences in efficacy or side effects demonstrated among the three formulations, patient preference for Kapanol over MST Continus" was observed.

A study by Toner et al., entitled, *Randomized, Double Blind, Phase III Crossover Study of a New Sustained-Release Oral Morphine Formulation, Kapanol Capsules,* evaluated the efficacy and side effects of Kapanol in comparison to immediate-release morphine where the former and latter were dosed every 12 and 4 hours respectively. It was concluded that "Kapanol, administered every 12 hours, provided effective and convenient control of cancer pain."

These above citations are meant to document that Kapanol has become recognized as a Q12H analgesic and as having a considerably slower rate of morphine release than MST Continus, and that this is presumed to provide superior analgesic therapy.

Another sustained-release oral morphine preparation for Q12H dosing is Oramorph® SR, previously referred to as Roxanol® SR. As with Kapanol, Oramorph SR has a-slower rate of morphine release, resulting in a lower maximal morphine concentration as evidenced in the following document: Hunt and Kaiko, *Comparison of the Pharmacokinetic Profiles of Two Oral Controlled-Release Morphine Formulations in Healthy Young Adults, Clinical Therapeutics,* Vol. 13, No. 41991.

It should be appreciated that these results have been interpreted as evidence of the superior clinical profile of Roxanol SR, based on its "smoother" time-concentration profile, relative to MS Contin. Indeed, the manufacturer, Roxane Laboratories, utilizes their steady-state comparison of Roxanol SR and MS Contin tablets in promotional materials, presumably to suggest that the smoother morphine time concentration curve and the minimal fluctuation between peak and trough morphine levels associated with Roxanol SR is a superior profile to that resulting from MS Contin tablet administration.

Inventors of the present invention have, however, within the context of two adequate and well controlled analgesic efficacy studies of MS Contin and Oramorph SR tablets demonstrated superior analgesic efficacy with comparable or fewer side effects with the use of MS Contin tablets as compared to the use of the Roxane Laboratory product: Bloomfield, et al., a manuscript entitled, *Analgesic Efficacy and Potency of Two Oral Controlled-Release Morphine Preparations,* from the April 1993 issue of *Clinical Pharmacology and Therapeutics.*

An orally administrable opioid formulation which would provide an extended duration of analgesia without higher incidence of adverse effects would be highly desirable. Such an oral sustained-release formulation of an opioid analgesic would be bioavailable and provide effective steady-state blood levels (e.g., plasma levels) of the drug when orally administered such that a duration of analgesic efficacy about 24 hours or more is obtained.

OBJECTS AND SUMMARY OF THE INVENTION

It is accordingly an object of the present invention to provide a method for treating patients in moderate to severe pain with an orally administered pharmaceutical dosage form of an opioid analgesic that is suitable for once-a-day administration.

It is yet another object of the present invention to provide a method for treating patients with a once-a-day opioid analgesic formulation which provides greater analgesic efficacy than that which is obtainable with the preferred Q12H analgesic therapies.

In accordance with the above objects and others which will be apparent from the further reading of the specification and of the appended claims, the present invention is related to the surprising discovery that in order to provide a 24 hour dosage form of an opioid analgesic, it is critical to provide the patient in pain with an analgesic preparation composed, in part, of a mechanism which would provide for an initially more rapid opioid release so that the minimum effective analgesic concentration can be more quickly approached in many patients who have measurable if not significant pain at the time of dosing.

The present invention is related in part to a method for providing effective pain management in humans for a time period of about 24 hours, comprising preparing a solid, controlled-release oral dosage form by incorporating an analgesically effective amount of an opioid analgesic into a controlled release dosage form which provides a rapid rate of initial rise of the plasma concentration of said opioid such that the peak plasma level of said opioid analgesic obtained in-vivo occurs from about 2 to about 8 hours after administration of the dosage form, and which provides large peak to trough fluctuations in opioid levels even after repeated dosing.

In certain preferred embodiments, the method further comprises including an portion of the dose of said opioid in immediate release form, said portion of said dose of said opioid being sufficient to provide loading dose of said opioid causing a significantly shortened $T_{max}$ and a large peak to trough fluctuation in said concentration of said opioid during said 24-hour efficacy period.

In certain preferred embodiments, the method further comprises providing said opioid formulation such that it exhibits first order release characteristics.

In certain preferred embodiments wherein the opioid is morphine, the maximum plasma concentration is from about 2 ng/ml to i5 about 14 ng/ml, and preferably is from about 3 ng/ml to about 8 ng/ml.

In other preferred embodiments, the method further comprises providing a formulation having an extended $T_{max}$, preferably for about 2 to about 4 hours.

The term "bioavailability" is defined for purposes of the present invention as the extent to which the drug (e.g., opioid analgesic) is absorbed from the unit dosage forms and becomes available at the site of drug action.

The terms "sustained release" and "extended duration" are defined for purposes of the present invention as the release of the drug (e.g., opioid analgesic) at such a rate that blood (e.g., plasma) levels are maintained within the therapeutic range but below toxic levels over a period of time of about 24 hours or longer.

BRIEF DESCRIPTION OF THE DRAWINGS

The following drawings are illustrative of embodiments of the invention and are not meant to limit the scope of the invention as encompassed by the claims.

DETAILED DESCRIPTION

Figure 1:
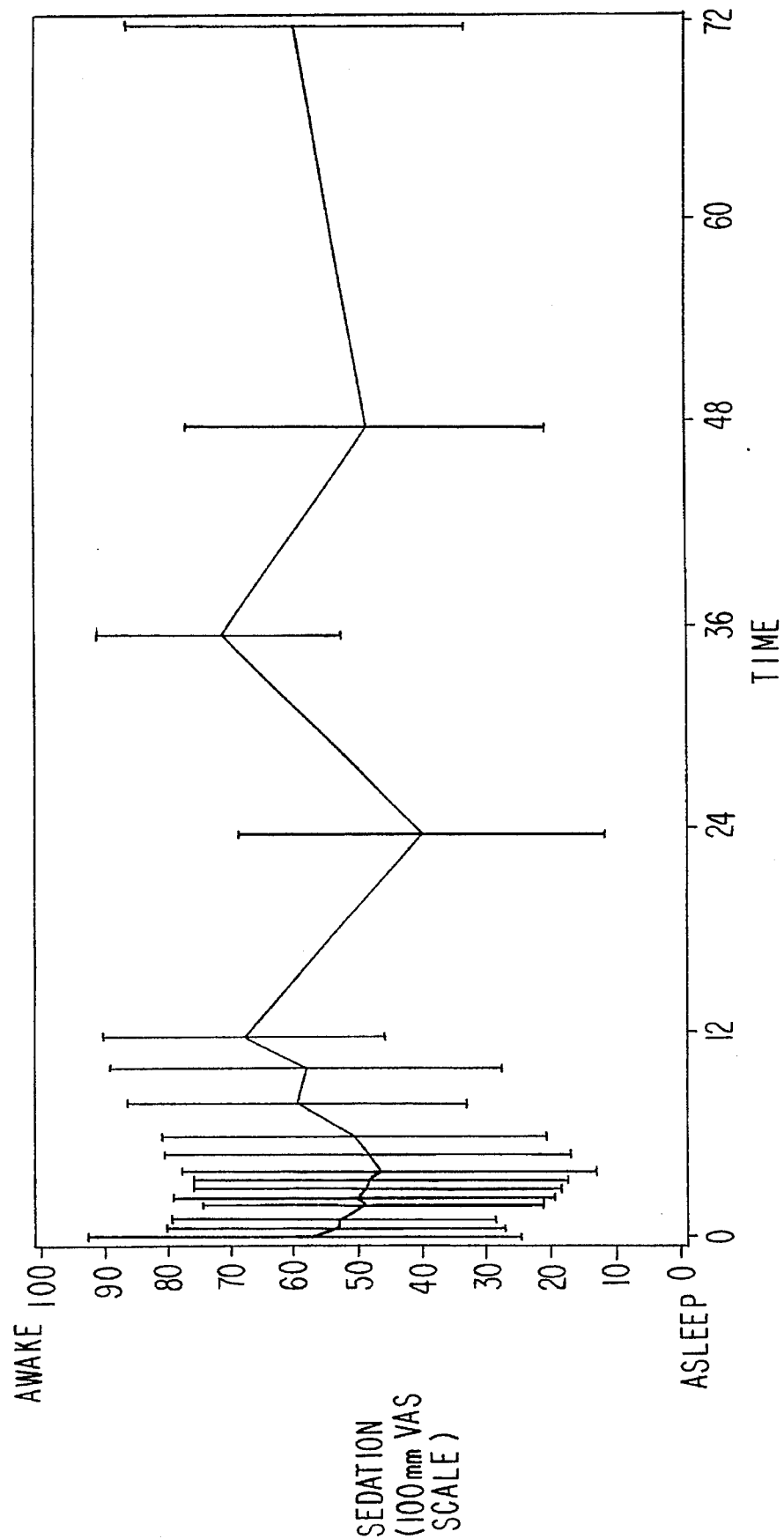
FIG. 1 is a graphical representation of the mean sedation vs. time curve for Example 1 (fasted)

Even at steady-state dosages of opioid analgesics, most patients remain in measurable or significant pain. The state-of-the-art approach to controlled release opioid therapy is to provide formulations which exhibit zero order pharmacokinetics and have minimal peak to trough fluctuation in opioid levels with repeated dosing. This zero order release provides very slow opioid absorption, and a generally flat serum concentration curve over time. A flat serum concentration curve is generally considered to be advantageous because it would in effect mimic a steady-state level where efficacy is provided but side effects common to opioid analgesics are minimized.

However, by formulating sustained release opioids in this manner, it has been discovered that the patients often experience considerable discomfort at about the time the next oral dose of the opioid is administered.

It has now been surprisingly discovered that quicker and greater analgesic efficacy is achieved by 24 hour oral opioid formulations which do not exhibit a substantially flat serum concentration curve, but which instead provide a more rapid initial opioid release so that the minimum effective analgesic concentration can be more quickly approached in many patients who have measurable if not significant pain at the time of dosing. Even at steady-state dosages of oral opioid analgesics, most patients have been found to remain in measurable or significant pain and would benefit greatly from treatment with the novel approach to oral opioid treatment disclosed herein. Also surprising and unexpected is the fact that while the methods of the present invention achieve quicker and greater analgesic efficacy, there is not a significantly greater incidence in side effects which would normally be expected as higher peak plasma concentrations occur.

One manner in which the method of the present invention is achieved is via the administration of oral sustained release opioid formulations which exhibit first order, rather than zero order, release characteristics.

Another manner in which the method of the present invention is achieved is via the administration of oral sustained release opioid formulations which exhibit relatively large peak to trough fluctuations in opioid levels, even after repeated dosing.

Yet another manner in which the method of the present invention is achieved is via the administration of oral sustained release opioid formulations which upon administration quickly release an effective portion of the opioid contained therein such that there is an initially more rapid opioid release so that the minimum effective analgesic concentration of the opioid can be more quickly achieved.

Defining effective analgesic plasma morphine levels is very complex. However, there is generally a "minimally effective analgesic concentration" (MEAC) of plasma morphine below which no analgesia is provided. While there is an indirect relationship between, e.g., plasma morphine levels and analgesia, higher plasma levels are generally associated with superior pain relief. There is a lag time or hysteresis, between the time of peak plasma morphine levels and the time of peak drug effects. This holds true for the treatment of pain with opioid analgesics in general.

The administration of 24-hour opioid oral sustained release formulations in accordance with the present invention reveals a greater degree of intensity of certain pharmacodynamic endpoints during the earlier portions of the plasma concentration curve (e.g., 4–8 hours after oral administration), such as sedation respiratory rate, pupil size, and/or combined scores from a questionnaire of opioid effects reported by the subjects at serial times following each treatment (i.e., administration of the oral dosage form). Other measures of analgesic efficacy such as sum of pain intensity difference (SPID) and total pain relief (TOTPAR) have consistently higher numerical scores via the presently claimed methods, while also generating in many cases fewer adverse events (which in general are predominantly mild or moderate somnolence, nausea and/or dizziness).

In certain preferred embodiments of the present invention, an effective amount of opioid in immediate release form is included in the 24 hour sustained release unit dose opioid formulation to be administered. The immediate release form of the opioid is included in an amount which is effective to shorten the time to maximum concentration of the opioid in the blood (e.g., plasma), such that the $T_{max}$ is shortened to a time of, e.g., from about 2 to about 4 hours. This causes the blood concentration curve to have an early peak rather than the substantially flattened curves currently recommended by those skilled in the art. It has been discovered that by including such an effective amount of immediate release opioid in the unit dose, the experience of relatively higher levels of pain in patients is significantly reduced. In such embodiments, an effective amount of the opioid in immediate release form may be coated onto the substrates of the present invention. For example, where the extended release opioid from the formulation is due to a controlled release coating, the immediate release layer would be overcoated on top of the controlled release coating. On the other hand, the immediate release layer may be coated onto the surface of substrates wherein the opioid is incorporated in a controlled release matrix. Where a plurality of the sustained release substrates comprising an effective unit dose of the opioid (e.g., multiparticulate systems including pellets, spheres, beads and the like) are incorporated into a hard gelatin capsule, the immediate release portion of the opioid dose may be incorporated into the gelatin capsule via inclusion of the sufficient amount of immediate release opioid as a powder or granulate within the capsule. Alternatively, the gelatin capsule itself may be coated with an immediate release layer of the opioid. One skilled in the art would recognize still other alternative manners of incorporating the immediate release opioid portion into the unit dose. Such alternatives are deemed to be encompassed by the appended claims.

Opioid analgesic compounds which may be used in the present invention include alfentanil, allylprodine, alphaprodine, anileridine, benzylmorphine, bezitramide, buprenorphine, butorphanol, clonitazene, codeine, cyclazocine, desomorphine, dextromoramide, dezocine, diampromide, dihydrocodeine, dihydromorphine, dimenoxadol, dimepheptanol, dimethylthiambutene, dioxaphetyl butyrate, dipipanone, eptazocine, ethoheptazine, ethylmethylthiambutene, ethylmorphine, etonitazene fentanyl, heroin, hydrocodone, hydromorphone, hydroxypethidine, isomethadone, ketobemidone, levallorphan, levorphanol, levophenacylmorphan, lofentanil, meperidine, meptazinol, metazocine, methadone, metopon, morphine, myrophine, nalbuphine, narceine, nicomorphine, norlevorphanol, normethadone, nalorphine, normorphine, norpipanone, opium, oxycodone, oxymorphone, papaveretum, pentazocine, phenadoxone, phenomorphan, phenazocine, phenoperidine, piminodine, piritramide, propheptazine, promedol, properidine, propiram, propoxyphene, sufentanil, tramadol, tilidine, salts thereof, mixtures of any of the foregoing, mixed mu-agonists/antagonists, mu-antagonist combinations, and the like. In certain preferred embodiments, the opioid analgesic is selected from the group consisting of hydromorphone, oxycodone, dihydrocodeine, codeine, dihydromorphine, morphine, buprenorphine, salts of any of the foregoing, and mixtures of any of the foregoing.

In one preferred embodiment the sustained-release opioid oral dosage form of the present invention includes hydromorphone as the therapeutically active ingredient in an amount from about 4 to about 64 mg hydromorphone hydrochloride. Alternatively, the dosage form may contain molar equivalent amounts of other hydromorphone salts or of the hydromorphone base. In another preferred embodiment, the opioid analgesic comprises morphine, and the sustained-release oral dosage forms of the present invention include form about 5 mg to about 800 mg morphine, by weight. In yet another preferred embodiment, the opioid analgesic comprises oxycodone, the sustained-release oral dosage forms of the present invention include from about 5 mg to about 400 mg oxycodone. In other preferred embodiments, the dosage form contains an appropriate amount of another of the opioid analgesics to provide a substantially equivalent therapeutic effect.

The sustained-release dosage forms of the present invention generally achieve and maintain therapeutic levels substantially without significant increases in the intensity and/or degree of concurrent side effects, such as nausea, vomiting or drowsiness, which are often associated with high blood levels of opioid analgesics. There is also evidence to suggest that the use of the present dosage forms leads to a reduced risk of drug addiction. Furthermore, the sustained-release dosage forms of the present invention preferably releases the opioid analgesic at a rate that is independent of pH, e.g., between pH 1.6 and 7.2. In other words, the dosage forms of the present invention avoid "dose dumping" upon oral administration.

In the present invention, the oral opioid analgesics have been formulated to provide for an increased duration of analgesic action allowing once-daily dosing. Surprisingly, these formulations, at comparable daily dosages of conventional immediate-release drug, are associated with a lower incidence in severity of adverse drug reactions and can also be administered at a lower daily dose than conventional oral medication while maintaining pain control.

In certain preferred embodiments of the present invention, the sustained-release opioid dosage forms comprise a plurality of substrates comprising the active ingredient, which substrates are coated with a sustained-release coating. The coating formulations of the present invention should be capable of producing a strong, continuous film that is smooth and elegant, capable of supporting pigments and other coating additives, non-toxic, inert, and tack-free.

In order to obtain a sustained-release of the opioid sufficient to provide an analgesic effect for the extended durations set forth in the present invention, the substrate comprising the therapeutically active agent may be coated with a sufficient amount of hydrophobic material to obtain a weight gain level from about 2 to about 30 percent, although the overcoat may be greater depending upon the physical properties of the particular opioid analgesic compound utilized and the desired release rate, among other things.

The solvent which is used for the hydrophobic material may be any pharmaceutically acceptable solvent, including water, methanol, ethanol, methylene chloride and mixtures thereof. It is preferable however, that the coatings be based upon aqueous dispersions of the hydrophobic material.

In certain preferred embodiments of the present invention, the hydrophobic polymer comprising the sustained-release coating is a pharmaceutically acceptable acrylic polymer, including but not limited to acrylic acid and methacrylic acid copolymers, methacrylic acid copolymers, methyl methacrylate copolymers, ethoxyethyl methacrylates, cynaoethyl methacrylate, methyl methacrylate, copolymers, methacrylic acid copolymers, methyl methacrylate copolymers, methyl methacrylate copolymers, methyl methacrylate copolymers, methacrylic acid copolymer, aminoalkyl methacrylate copolymer, methacrylic acid copolymers, methyl methacrylate copolymers, poly(acrylic acid), poly(methacrylic acid, methacrylic acid alkylamide copolymer, poly(methyl methacrylate), poly(methacrylic acid) (anhydride), methyl methacrylate, polymethacrylate, methyl methacrylate copolymer, poly(methyl methacrylate), poly(methyl methacrylate) copolymer, polyacrylamide, aminoalkyl methacrylate copolymer, poly(methacrylic acid anhydride), and glycidyl methacrylate copolymers.

In certain preferred embodiments, the acrylic polymer is comprised of one or more ammonio methacrylate copolymers. Ammonio methacrylate copolymers are well known in the art, and are described in NF XVII as fully polymerized copolymers of acrylic and methacrylic acid esters with a low content of quaternary ammonium groups.

In one preferred embodiment, the acrylic coating is an acrylic resin lacquer used in the form of an aqueous dispersion, such as that which is commercially available from Rohm Pharma under the Tradename Eudragit®. In further preferred embodiments, the acrylic coating comprises a mixture of two acrylic resin lacquers commercially available from Rohm Pharma under the Tradenames Eudragit® RL 30 D and Eudragit® RS 30 D, respectively. Eudragit® RL 30 D and Eudragit® RS 30 D are copolymers of acrylic and methacrylic esters with a low content of quaternary ammonium groups, the molar ratio of ammonium groups to the remaining neutral (meth)acrylic esters being 1:20 in Eudragit® RL 30 D and 1:40 in Eudragit® RS 30 D. The mean molecular weight is about 150,000. The code designations RL (high permeability) and RS (low permeability) refer to the permeability properties of these agents. Eudragit® RL/RS mixtures are insoluble in water and in digestive fluids. However, coatings formed from the same are swellable and permeable in aqueous solutions and digestive fluids.

The Eudragit® RL/RS dispersions of the present invention may be mixed together in any desired ratio in order to ultimately obtain a sustained-release formulation having a desirable dissolution profile. Desirable sustained-release formulations may be obtained, for instance, from a retardant coating derived from 100% Eudragit® RL, 50% Eudragit® RL and 50% Eudragit® RS, and 10% Eudragit®

RL:Eudragit® 90% RS. Of course, one skilled in the art will recognize that other acrylic polymers may also be used, such as, for example, Eudragit® L.

In other preferred embodiments, the hydrophobic polymer which may be used for coating the substrates of the present invention is a hydrophobic cellulosic material such as ethylcellulose. Those skilled in the art will appreciate that other cellulosic polymers, including other alkyl cellulosic polymers, may be substituted for part or all of the ethylcellulose included in the hydrophobic polymer coatings of the present invention.

One commercially-available aqueous dispersion of ethylcellulose is Aquacoat® (FMC Corp., Philadelphia, Pa., U.S.A.). Aquacoat® is prepared by dissolving the ethylcellulose in a water-immiscible organic solvent and then emulsifying the same in water in the presence of a surfactant and a stabilizer. After homogenization to generate submicron droplets, the organic solvent is evaporated under vacuum to form a pseudolatex. The plasticizer is not incorporated in the pseudolatex during the manufacturing phase. Thus, prior to using the same as a coating, it is necessary to intimately mix the Aquacoat® with a suitable plasticizer prior to use.

Another aqueous dispersion of ethylcellulose is commercially available as Surelease® (Colorcon, Inc., West Point, Pa., U.S.A.). This product is prepared by incorporating plasticizer into the dispersion during the manufacturing process. A hot melt of a polymer, plasticizer (dibutyl sebacate), and stabilizer (oleic acid) is prepared as a homogeneous mixture, which is then diluted with an alkaline solution to obtain an aqueous dispersion which can be applied directly onto substrates.

In embodiments of the present invention where the coating comprises an aqueous dispersion of a hydrophobic polymer, the inclusion of an effective amount of a plasticizer in the aqueous dispersion of hydrophobic polymer will further improve the physical properties of the film. For example, because ethylcellulose has a relatively high glass transition temperature and does not form flexible films under normal coating conditions, it is necessary to plasticize the ethylcellulose before using the same as a coating material. Generally, the amount of plasticizer included in a coating solution is based on the concentration of the film-former, e.g., most often from about 1 to about 50 percent by weight of the film-former. Concentration of the plasticizer, however, can only be properly determined after careful experimentation with the particular coating solution and method of application.

Examples of suitable plasticizers for ethylcellulose include water insoluble plasticizers such as dibutyl sebacate, diethyl phthalate, triethyl citrate, tibutyl citrate, and triacetin, although it is possible that other water-insoluble plasticizers (such as acetylated monoglycerides, phthalate esters, castor oil, etc.) may be used. Triethyl citrate is especially preferred.

Examples of suitable plasticizers for the acrylic polymers of the present invention include citric acid esters such as triethyl citrate NF XVI, tributyl citrate, dibutyl phthalate, and possibly 1,2-propylene glycol, polyethylene glycols, propylene glycol, diethyl phthalate, castor oil, and triacetin, although it is possible that other water-insoluble plasticizers (such as acetylated monoglycerides, phthalate esters, castor oil, etc.) may be used. Triethyl citrate is especially preferred.

The sustained-release profile of the formulations of the invention can be altered, for example, by varying the thickness of the hydrophobic coating, changing the particular hydrophobic material used, or altering the relative amounts of, e.g., different acrylic resin lacquers, altering the manner in which the plasticizer is added (e.g., when the sustained-release coating is derived from an aqueous dispersion of hydrophobic polymer), by varying the amount of plasticizer relative to hydrophobic polymer, by the inclusion of additional ingredients or excipients, by altering the method of manufacture, etc.

Sustained-release spheroids or beads, coated with a therapeutically active agent are prepared, e.g. by dissolving the opioid analgesic in water and then spraying the solution onto a substrate, for example, nu pariel 18/20 beads, using a Wuster insert. Optionally, additional ingredients are also added prior to coating the beads in order to assist the hydromorphone binding to the substrates, and/or to color the solution, etc. For example, a product which includes hydroxypropyl methylcellulose, etc. with or without colorant may be added to the solution and the solution mixed (e.g., for about 1 hour) prior to application of the same onto the beads. The resultant coated substrate, in this example beads, may then be optionally overcoated with a barrier agent, to separate the therapeutically active agent from the hydrophobic sustained-release coating. An example of a suitable barrier agent is one which comprises hydroxypropyl methylcellulose. However, any film-former known in the art may be used. It is preferred that the barrier agent does not affect the dissolution rate of the final product.

The hydromorphone, HPMC protected (optional) beads may then be overcoated with hydrophobic polymer, preferably with an effective amount of plasticizer.

The coating solutions of the present invention preferably contain, in addition to the film-former, plasticizer, and solvent system (i.e., water), a colorant to provide elegance and product distinction. Color may be added to the solution of the therapeutically active agent instead, or in addition to the aqueous dispersion of hydrophobic polymer.

The plasticized aqueous dispersion of hydrophobic polymer may be applied onto the substrate comprising the therapeutically active agent by spraying using any suitable spray equipment known in the art. In a preferred method, a Wurster fluidized-bed system is used in which an air jet, injected from underneath, fluidizes the core material and effects drying while the acrylic polymer coating is sprayed on. A sufficient amount of the aqueous dispersion of hydrophobic polymer to obtain a predetermined sustained-release of said therapeutically active agent when said coated substrate is exposed to aqueous solutions, e.g. gastric fluid, is preferably applied, taking into account the physically characteristics of the therapeutically active agent, the manner of incorporation of the plasticizer, etc. After coating with the hydrophobic polymer, a further overcoat of a film-former such as Opadry® is optionally applied to the beads. This overcoat is provided, if at all, in order to substantially reduce agglomeration of the beads.

Next, the coated beads are cured in order to obtain a stabilized release rate of the therapeutically active agent.

When the coating comprises an aqueous dispersion of ethylcellulose, the coated substrate is preferably subjected to curing at a temperature greater than the glass transition temperature of the coating solution (i.e., ethylcellulose) and at a relative humidity from about 60% to about 100%, until the curing endpoint is reached, e g., about 60° C. and a relative humidity from about 60% to about 100% for a time period from about 48 to about 72 hours.

In preferred embodiments of the present invention directed to the acrylic coating, a stabilized product is obtained by subjecting the coated substrate to oven curing at a temperature above the Tg of the plasticized acrylic polymer for the required time period, the optimum values for temperature and time for the particular formulation being determined experimentally. In certain embodiments of the present invention, the stabilized product is obtained via an oven curing conducted at a temperature of about 45° C. for a time period from about 24 to about 48 hours or longer.

The release of the therapeutically active agent from the sustained-release formulation of the present invention can be further influenced, i.e., adjusted to a desired rate, by the addition of one or more release-modifying agents, or by providing one or more passageways through the coating. The ratio of hydrophobic polymer to water soluble material is determined by, among other factors, the release rate required and the solubility characteristics of the materials selected.

The release-modifying agents which function as pore-formers may be organic or inorganic, and include materials that can be dissolved, extracted or leached from the coating in the environment of use. The pore-formers may comprise one or more hydrophilic polymers such as hydroxypropylmethylcellulose.

The sustained-release coatings of the present invention can also include erosion-promoting agents such as starch and gums.

The sustained-release coatings of the present invention can also include materials useful for making microporous lamina in the environment of use, such as polycarbonates comprised of linear polyesters of carbonic acid in which carbonate groups reoccur in the polymer chain.

The release-modifying agent may also comprise a semi-permeable polymer.

In certain preferred embodiments, the release-modifying agent is selected from hydroxypropylmethylcellulose, lactose, metal stearates, and mixtures of any of the foregoing.

The sustained-release coatings of the present invention may also include an exit means comprising at least one passageway, orifice, or the like. The passageway may be formed by such methods as those disclosed in U.S. Pat. Nos. 3,845,770; 3,916,889; 4,063,064; and 4,088,864 (all of which are hereby incorporated by reference). The passageway can have any shape such as round, triangular, square, elliptical, irregular, etc.

In other embodiments of the present invention, the present invention may utilize a multiparticulate sustained-release matrix. Suitable materials for inclusion in a sustained-release matrix are (a) Hydrophilic polymers, such as gums, cellulose ethers, acrylic resins and protein derived materials. Of these polymers, the cellulose ethers, especially hydroxyalkylcelluloses and carboxyalkylcelluloses, are preferred. The oral dosage form may contain between 1% and 80% (by weight) of at least one hydrophilic or hydrophobic polymer.

(b) Digestible, long chain ($C_8$-$C_{50}$, especially $C_{12}$-$C_{40}$), substituted or unsubstituted hydrocarbons, such as fatty acids, fatty alcohols, glyceryl esters of fatty acids, mineral and vegetable oils and waxes. Hydrocarbons having a melting point of between 25° and 90° C. are preferred. Of these long chain hydrocarbon materials, fatty (aliphatic) alcohols are preferred. The oral dosage form may contain up to 60% (by weight) of at least one digestible, long chain hydrocarbon.

(c) Polyalkylene glycols. The oral dosage form may contain up to 60% (by weight) of at least one polyalkylene glycol.

For example, a suitable matrix may be one which comprises at least one water soluble hydroxyalkyl cellulose, at least one $C_{12}$-$C_{36}$, preferably $C_{14}$-$C_{22}$, aliphatic alcohol and, optionally, at least one polyalkylene glycol. The at least one hydroxyalkyl cellulose is preferably a hydroxy ($C_1$ to $C_6$) alkyl cellulose, such as hydroxypropylcellulose, hydroxypropylmethylcellulose and, especially, hydroxyethyl cellulose. The amount of the at least one hydroxyalkyl cellulose in the present oral dosage form will be determined, inter alia, by the precise rate of opioid release required. The at least one aliphatic alcohol may be, for example, lauryl alcohol, myristyl alcohol or stearyl alcohol. In certain preferred embodiments, the at least one aliphatic alcohol is cetyl alcohol or cetostearyl alcohol. The amount of the at least one aliphatic alcohol in the present oral dosage form will be determined, as above, by the precise rate of opioid release required. It will also depend on whether at least one polyalkylene glycol is present in or absent from the oral dosage form. In the absence of at least one polyalkylene glycol, the oral dosage form preferably contains between 20% and 50% (by wt) of the at least one aliphatic alcohol. When at least one polyalkylene glycol is present in the oral dosage form, then the combined weight of the at least one aliphatic alcohol and the at least one polyalkylene glycol preferably constitutes between 20% and 50% (by wt) of the total dosage.

In one embodiment, the ratio of, e.g., at least one hydroxyalkyl cellulose or acrylic resin to at least one aliphatic alcohol/polyalkylene glycol determines, to a considerable extent, the release rate of the opioid from the formulation. A ratio of the at least one hydroxyalkyl cellulose to at least one aliphatic alcohol/polyalkylene glycol of between 1:2 and 1:4 is preferred, with a ratio of between 1:3 and 1:4 being particularly preferred.

At least one polyalkylene glycol may be, for example, polypropylene glycol or, preferably, polyethylene glycol. The number average molecular weight of the at least one polyalkylene glycol is preferred between 1000 and 15000 especially between 1500 and 12000.

Another suitable sustained-release matrix would comprise an alkylcellulose (especially ethyl cellulose), a $C_{12}$ to $C_{36}$ aliphatic alcohol and, optionally, a polyalkylene glycol.

In addition to the above ingredients, a sustained-release matrix may also contain suitable quantities of other materials, e.g., diluents, lubricants, binders, granulating aids, colorants, flavorants and glidants that are conventional in the pharmaceutical art.

In order to facilitate the preparation of a solid, sustained-release oral dosage form according to this invention there is provided, in a further aspect of the present invention, a process for the preparation of a solid, sustained-release oral dosage form according to the present invention comprising incorporating opioids or a salt thereof in a sustained-release matrix. Incorporation in the matrix may be effected, for example, by (a) forming granules comprising at least one water soluble hydroxyalkyl cellulose and opioid or an opioid salt, (b) mixing the hydroxyalkyl cellulose containing granules with at least one $C_{12}$-$C_{36}$ aliphatic alcohol, and (c) optionally, compressing and shaping the granules. Preferably, the granules are formed by wet granulating the hydroxyalkyl cellulose/opioid with water. In a particularly preferred embodiment of this process, the amount of water added during the wet granulation step is preferably between 1.5 and 5 times, especially between 1.75 and 3.5 times, the dry weight of the opioid.

In yet other alternatives embodiments, a spheronizing agent, together with the active ingredient can be spheronized to form spheroids. Microcrystalline cellulose is preferred. A suitable microcrystalline cellulose is, for example, the material sold as Avicel PH 101 (Trade Mark, FMC Corporation). In such embodiments, in addition to the active ingredient and spheronizing agent, the spheroids may also contain a binder. Suitable binders, such as low viscosity, water soluble polymers, will be well known to those skilled in the pharmaceutical art. However, water soluble hydroxy lower alkyl cellulose, such as hydroxy propyl cellulose, are preferred. Additionally (or alternatively) the spheroids may contain a water insoluble polymer, especially an acrylic polymer, an acrylic copolymer, such as a methacrylic acid-ethyl acrylate copolymer, or ethyl cellulose. In such embodiments, the sustained-release coating will generally include a water insoluble material such as (a) a wax, either alone or in admixture with a fatty alcohol; or (b) shellac or zein.

The substrates of the present invention may also be prepared via a melt pellitization technique. In such circumstance, the opioid in finely divided form is combined with a binder (also in particulate form) and other optional inert ingredients, and thereafter the mixture is pelletized, e.g., by mechanically working the mixture in a high shear mixer to form the pellets (granules, spheres). Thereafter, the pellets (granules, spheres) may be sieved in order to obtain pellets of the requisite size. The binder material is preferably in particulate form and has a melting point above about 40° C. Suitable binder substances include, for example, hydrogenated castor oil, hydrogenated vegetable oil, other hydrogenated fats, fatty alcohols, fatty acid esters, fatty acid glycerides, and the like.

DETAILED DESCRIPTION OF THE PREFERRED EMBODIMENTS

The following examples illustrate various aspects of the present invention. They are not to be construed to limit the claims in any manner whatsoever.

EXAMPLES 1–2

In Example 1, morphine sulfate sustained-release beads with a 5% w/w sustained-release coating comprising Eudragit® RS were prepared, including a 10% immediate release morphine sulfate overcoat. In Example 2, morphine sulfate sustained-release beads with a 8% w/w sustained-release coating comprising Eudragit® RS were prepared, including a 10% immediate release morphine sulfate overcoat.

Morphine sulfate beads were first manufactured using a rotor processing technique. The formula of the morphine sulfate beads to which the sustained-release coating was applied is set forth in Table 1 below:

TABLE 1

| Ingredient | Amt/Unit (mg) | Percent (%) |
| --- | --- | --- |
| Morphine Sulfate Powder | 30 mg | 14.3% |
| Lactose Hydrous Impalpable | 42.5 mg | 20.2% |
| PVP | 2.5 mg | 1.2% |
| Sugar Beads 18/20 | 125 mg | 59.4% |
| Purified Water | qs mg | — |
| Opadry Red YS-1-1841 | 10.5 mg | 4.9% |

TABLE 1-continued

| Ingredient | Amt/Unit (mg) | Percent (%) |
| --- | --- | --- |
| Total | 210.5 mg | 100.0% |

A sustained-release coating was then applied to the morphine sulfate beads. The formula for the sustained release coating of Examples 1 and 2 is set forth in Table 2 below:

TABLE 2

| Ingredient | Example 1 (mg) | % | Example 2 (mg) | % |
| --- | --- | --- | --- | --- |
| Morphine Base Beads | 189.45 mg | 86.7% | 189.5 mg | 83.0% |
| Retardant Coating | | | | |
| Eudragit RS 30D | 9.5 mg | 4.3% | 15.2 mg | 6.7% |
| Triethyl Citrate | 1.9 mg | 0.9% | 3.0 mg | 1.3% |
| Talc | 3.8 mg | 1.7% | 6.1 mg | 2.7% |
| Purified Water | qs | — | qs | — |
| Overcoat | | | | |
| Morphine Sulfate Powder | 3.0 mg | 1.4% | 3.0 mg | 1.3% |
| Opadry Red YS-1-1841 | 10.8 mg | 5.0% | 11.4 mg | 5.0% |
| Purified Water | qs | — | qs | — |
| Total | 218.45 mg | 100.0% | 228.2 mg | 100.0% |

The sustained-release coating was manufactured as follows. The Eudragit RS 30D was plasticized with triethyl citrate and talc for approximately 30 minutes. A load of the morphine sulfate beads was charged into a Wurster Insert of a Glatt equipped with a 1.2 mm spray nozzle and the beads were coated to a weight gain of 5% and 8% for Examples 1 and 2, respectively. The final protective Opadry dispersion overcoat was then applied in the Wurster Insert. Upon completion the beads were cured for two days in a dry oven of 45° C. The cured beads were then filled into gelatin capsules at a 30 mg strength.

Dissolution testing was conducted on the gelatin capsules via U.S.P. Apparatus II (Paddle Method). The capsules were placed into 700 ml of simulated gastric fluid (without enzymes) for the first hour at 100 rpm and 37° C., and then placed into 900 ml of simulated gastric fluid (without enzymes) after the first hour. The results of the percent of morphine sulfate dissolved in relation to time for Examples 1 and 2 are set forth in Table 3 below:

TABLE 3

| | Percent Morphine Sulfate Dissolved | |
| --- | --- | --- |
| Time | Example 1 | Example 2 |
| 1 hour | 11.9% | 10.2% |
| 2 hours | 15.4% | 11.3% |
| 4 hours | 28.1% | 12.8% |
| 8 hours | 58.3% | 16.4% |
| 12 hours | 79.2% | 29.6% |
| 18 hours | 92.0% | 58.1% |
| 24 hours | 96.6% | 73.2% |

Clinical Evaluation of Examples 1–2

Ten normal, healthy male subjects were enrolled in a four-way, randomized, single-dose, crossover pharmacokinetic/pharmacodynamic study to characterize the effect of food on the pharmacokinetic/ pharmacodynamic profile of Example 1 compared with the same product and with morphine CR 30 mg tablet (MS Contin®), each in the fasted state, using plasma morphine concentration and pharmacodynamic parameters. A comparison of Example 2 with morphine CR 30 mg tablet (MS Contin®) was also made. Plasma morphine concentrations were used for calculation of pharmacokinetic parameters including: (a) absorption and elimination rates; (b) area under the curve (AUC); (c) maximum plasma concentration ($C_{max}$); (d) time to maximum plasma concentration $T_{max}$); (e) $T_{1/2}$ (elimination). Pharmacodynamic effect compared with plasma concentrations of morphine was to be described from data obtained from the following pharmacodynamic parameters: mood, sedation, respiratory rate, pupillometry and an adjective questionnaire.

Clinical Laboratory Evaluations

Blood samples were collected for hematology (hemoglobin, hematocrit, red blood cell count, white blood cell count with differential, platelet count) and blood chemistry analyses (calcium, inorganic phosphate, uric acid, total protein, albumin, cholesterol, alkaline phosphatase, lactate dehydrogenase (LDH), total bilirubin, serum glutamic oxaloacetic transaminase (SGOT), serum glutamic pyruvate transaminase (SGPT), fasting blood glucose, blood urea nitrogen (BUN), serum creatinine) pre- and post- (72 hours) study (i.e., 72 hours after Phase 4 dose). A urine sample was collected for urinalysis (specific gravity, glucose, albumin, bile, pH, acetone, microscopic examination) pre- and post- (72 hours) study (i.e., 72 hours after Phase 4 dose). A pre-study urinalysis for illicit drugs was performed during the screening process and immediately pre-dose for each administration of the study drug (Day 1 of Phases 1 through 4).

Plasma morphine concentrations were determined from blood samples which were drawn just prior to dosing (0 hour) and thereafter at 0.5, 1, 2, 2.5, 3, 3.5, 4, 5, 6, 8, 10, 12, 18, 24, 36, 48 and 72 hours following each dose. Blood samples, each approximately 10 ml, were drawn into tubes containing ethylenediaminetetraacetic acid (EDTA) solution, an anticoagulant. Following centrifugation, the plasma was pipetted into two 5-ml polypropylene, labeled tubes and frozen at −20° C. One set of samples was shipped to the designated analytical laboratory in sufficient dry ice to keep them frozen for 2 days, and the second set was retained frozen at the study site as a back-up.

Pharmacodynamic Measurements

Measurements of the following pharmacodynamic parameters were made just prior to blood sampling at baseline (within 30 minutes prior to dosing) and thereafter at 0.5, 1, 2, 2.5, 3, 3.5, 4, 5, 6, 8, 10, 12, 18, 24, 36, 48 and 72 hours following each dose.

Mood (measured by a visual analog scale (VAS) on a subject diary sheet)—10 minutes prior to blood sampling. The VAS was anchored on one end as Worst Mood and the other end as Best Mood.

Sedation (measured by VAS on a subject diary sheet)—10 minutes prior to blood sampling. The VAS was anchored on one end as Asleep and the other end as Awake.

Respiratory rate (breaths per minute)—within 5 minutes of blood sampling. (Data were recorded on a subject diary sheet.)

Pupil size— measured by pupillometry—within 5 minutes of blood sampling. Only the left eye was measured at all time periods. (Data were recorded on a subject diary sheet.)

Figure 2:
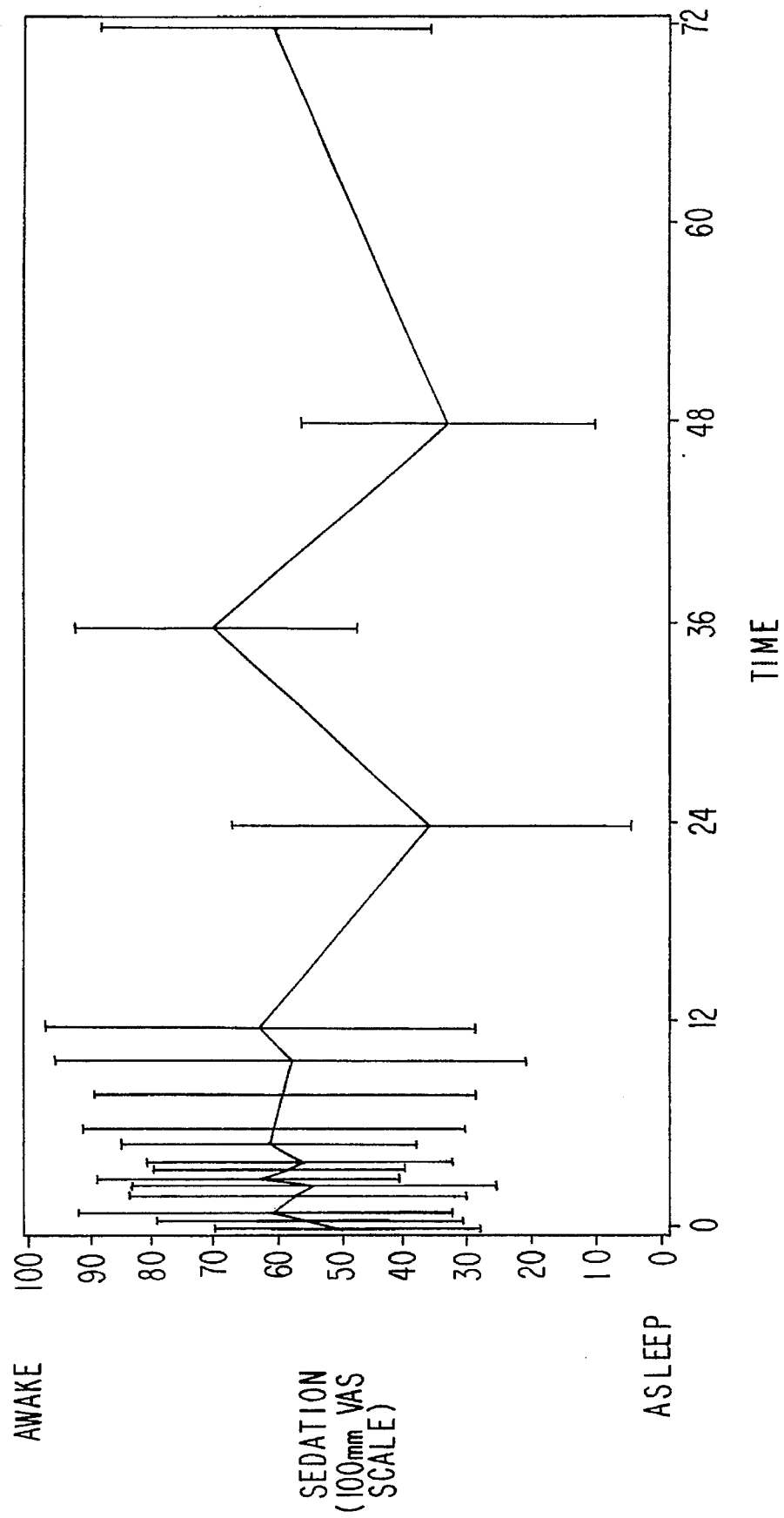
FIG. 2 is a graphical representation of the mean sedation vs. time curve for Example 2 (fasted)
Figure 3:
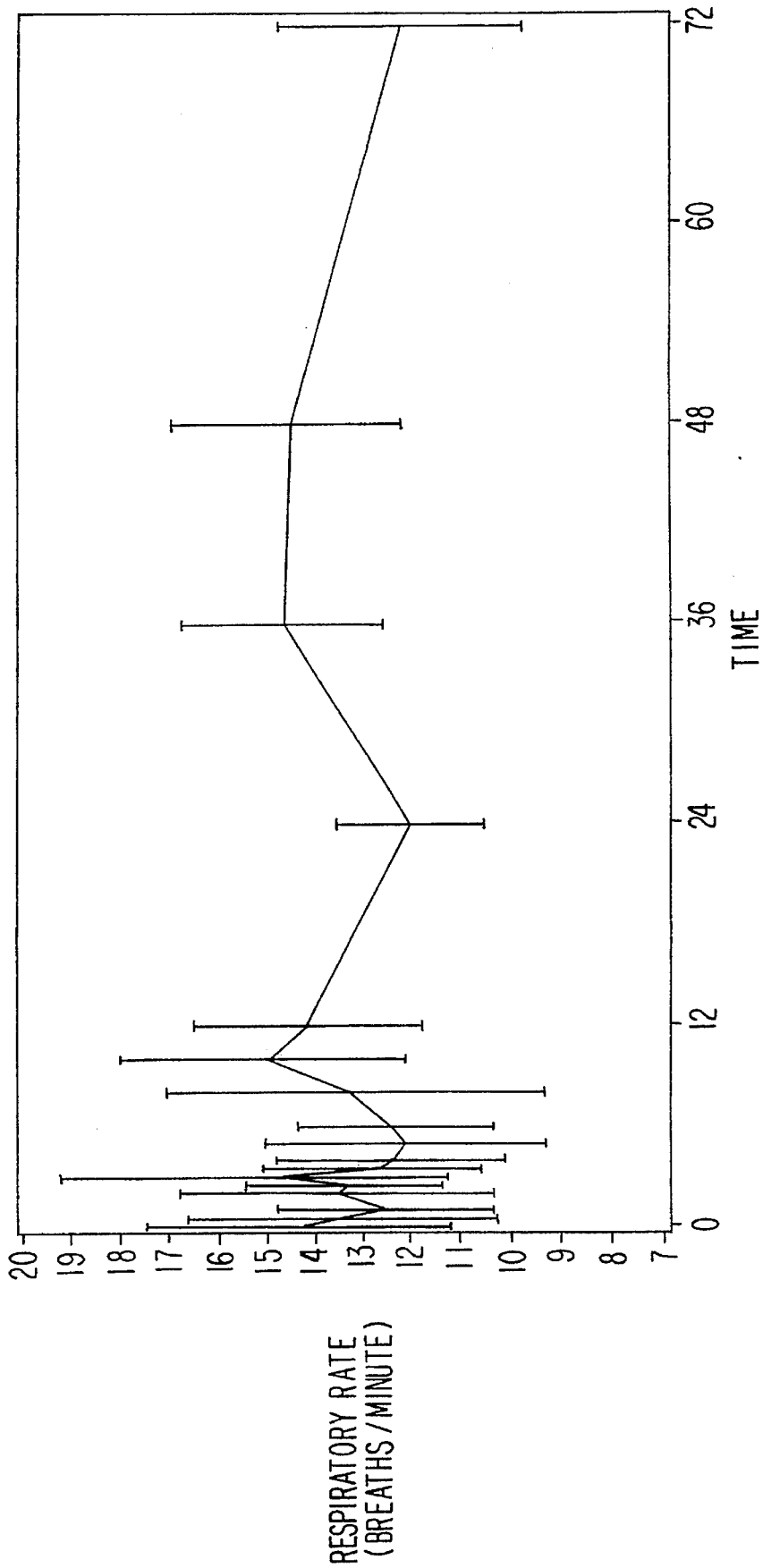
FIG. 3 is a graphical representation of the mean respiratory rate vs. time curve for Example 1 (fasted)
Figure 4:
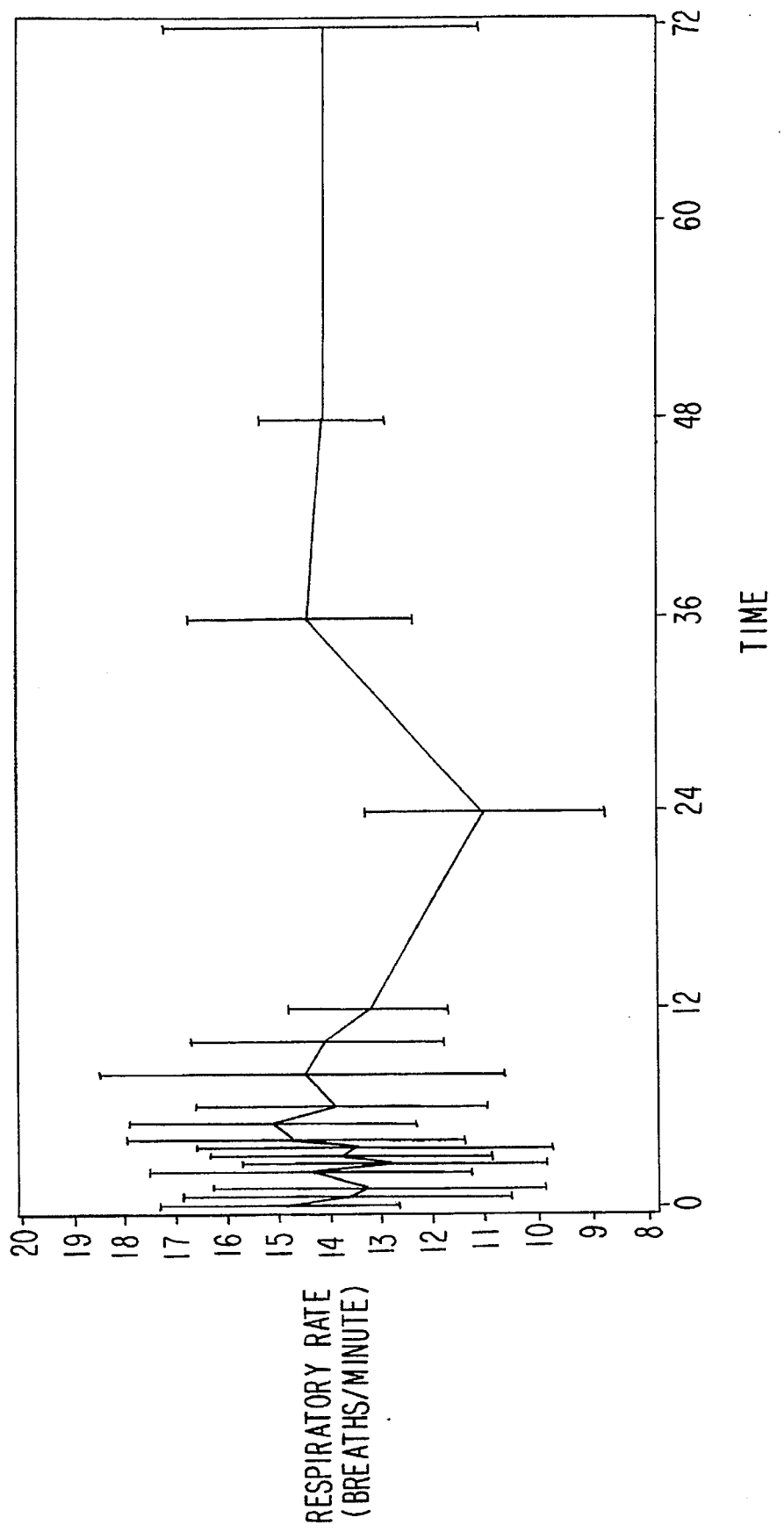
FIG. 4 is a graphical representation of the mean respiratory rate vs. time curve for Example 2 (fasted)

FIG. 1 is a graphical representation of the mean sedation vs. time curve for Example 1 (fasted). FIG. 2 is a graphical representation of the mean sedation vs. time curve for Example 2 (fasted). FIG. 3 is a graphical representation of the mean respiratory rate vs. time curve for Example 1 (fasted). FIG. 4 is a graphical representation of the mean respiratory rate vs. time curve for Example 2 (fasted).

Plasma morphine concentrations were determined by a high-performance liquid chromatographic procedure. Arithmetic mean Cmax, Tmax, AUC, half-lives calculated from individual plasma morphine concentration-versus-time, and oral bioavailability data were as set forth in Tables 1A and 1B below:

TABLE 1A

| Pharmaco-kinetic Ex. 1 Parameter | MS Contin ® (Fast) | Ex. 2 (Fast) | Ex. 2 (Fast) | Ex. 1 (Fed) |
|---|---|---|---|---|
| $C_{max}$ (ng/ml) | 13.05 | 3.95* | 5.42* | 5.87* |
| $T_{max}$ (hours) | 2.45 | 15.05* | 5.85 | 6.90 |
| AUC (0.72) (hr-ng/ml) | 101.11 | 136.10* | 109.37 | 111.33 |
| AUC (0,00) (hr-ng/ml) | 101.31 | 155.44* | 117.77 | 114.45 |
| $T_{1/2}$(elim; hrs) | 2.81 | 89.68* | 19.02 | 10.34 |
| $T_{1/2}$(abs; hrs) | 1.20 | 3.96 | 2.51 | 3.48 |

TABLE 1B (A = MS Contin; B = Example 2 fasted; C = Example 1 Fed; and D = Example 1 fasted)

| Pharmaco-kinetic Parameter | $F_0$ (%) 90% C.I. (B vs. A) | $F_0$ (%) 90% C.I. (C vs. A) | $F_0$ (%) 90% C.I. (D vs. A) | $F_0$ (%) 90% C.I. (D vs. C) |
|---|---|---|---|---|
| $C_{max}$ (ng/ml) | 32.24 (15.7–48.7) | 39.88 (23.3–56.5) | 42.50 (26.0–59.0) | 106.57 (65.2–148.0) |
| $T_{max}$ (hours) | 608.27 (435.6–780.9) | 232.33 (58.8–405.8) | 290.48 (117.9–463.11) | 125.03 (50.7–199.3) |
| AUC (0.72) (hr-ng/ml) | 134.53 (111.1–158.0) | 105.02 (81.5–128.6) | 106.04 (82.6–129.5) | 100.97 (78.6–123.3) |
| AUC (0,00) (hr-ng/ml) | 151.04 (112.6–189.4) | 112.91 (81.8–144.0) | 108.09 (77.1–139.0) | 95.73 (68.3–123.1) |
| $T_{1/2}$(elim; hrs) | 3076.7 (2256.7–3896.7) | 689.41 (24.9–1353.9) | 374.01 (−286.8–1034.9) | 54.25 (−41.6–150.1) |
| $T_{1/2}$(abs; hrs) | 281.21 (−123.1–685.5) | 167.18 (−11.7–346.0) | 239.86 (62.4–417.3) | 143.48 (37.2–249.8) |

*Statistically significant (p<.0500) when compared to MS Contin ® (based on untransformed data)
$F_0$ (%) = oral bioavailability (Test least squares mean/Reference least squares mean)

Table 2 provides the mean (± S.D.) plasma morphine concentrations (ng/ml) following dosing with MS Contin® and Examples 1 and 2.

TABLE 2

Mean (± S.D.) Plasma Morphine
Concentrations (ng/ml) Following Dosing With
MS Contin ® And Each Formulation Of Morphine Beads

| Time (hours) | MS Contin ® 30 mg (Fast) | Ex. 2 (Fast) | Ex. 1 (Fast) | Ex. 1 (Fed) |
|---|---|---|---|---|
| 0.00 | 0.00 ± 0.00 | 0.00 ± 0.00 | 0.00 ± 0.00 | 0.00 ± 0.00 |
| 0.50 | 3.04 ± 2.07 | 2.22 ± 1.09 | 1.82 ± 1.35 | 0.51 ± 0.79 |
| 1.00 | 6.78 ± 4.19 | 1.89 ± 0.54 | 2.09 ± 1.07 | 1.46 ± 0.95 |
| 2.00 | 11.43 ± 5.70 | 1.60 ± 0.69 | 2.33 ± 0.98 | 2.46 ± 0.91 |
| 2.50 | 10.30 ± 6.46 | 1.78 ± 1.16 | 2.22 ± 0.88 | 2.51 ± 0.88 |
| 3.00 | 9.40 ± 5.41 | 1.54 ± 0.97 | 2.61 ± 1.12 | 3.47 ± 1.77 |
| 3.50 | 8.09 ± 4.48 | 1.34 ± 0.98 | 2.82 ± 1.39 | 3.03 ± 1.26 |
| 4.00 | 7.11 ± 3.78 | 1.06 ± 0.49 | 3.60 ± 2.50 | 3.41 ± 1.82 |
| 5.00 | 7.25 ± 4.71 | 1.54 ± 1.21 | 4.09 ± 2.24 | 3.80 ± 1.29 |
| 6.00 | 5.27 ± 3.31 | 1.20 ± 0.77 | 4.11 ± 1.74 | 4.23 ± 1.68 |
| 8.00 | 3.19 ± 1.99 | 1.58 ± 1.00 | 3.80 ± 1.46 | 4.46 ± 1.51 |
| 10.0 | 1.87 ± 1.00 | 2.62 ± 1.05 | 3.57 ± 1.44 | 4.16 ± 1.37 |
| 12.0 | 1.70 ± 0.76 | 3.10 ± 1.64 | 2.83 ± 0.64 | 4.33 ± 2.20 |
| 18.0 | 1.23 ± 0.67 | 3.04 ± 1.11 | 2.40 ± 1.13 | 1.85 ± 1.12 |
| 24.0 | 1.38 ± 0.96 | 2.54 ± 0.55 | 1.82 ± 1.01 | 1.71 ± 0.73 |
| 36.0 | 0.85 ± 0.64 | 2.58 ± 1.04 | 1.35 ± 0.70 | 1.19 ± 0.40 |
| 48.0 | 0.22 ± 0.47 | 1.48 ± 0.48 | 0.69 ± 1.08 | 0.73 ± 0.56 |
| 72.0 | 0.05 ± 0.16 | 0.54 ± 0.66 | 0.16 ± 0.33 | 0.22 ± 0.46 |

Table 3 provides the mean (± S.D.) pharmacokinetic parameters following dosing with MS Contin® And Examples 1–2.

TABLE 3

Mean (± S.D.) Pharmacokinetic
Parameters Following Dosing With
MS Contin ® And Each Formulation Of Morphine Beads

| Parameter | MS Contin ® 30 mg (Fast) | Ex. 2 (Fast) | Ex. 1 (Fast) | Ex. 1 (Fed) |
|---|---|---|---|---|
| $C_{max}$ (ng/ml) | 13.05 ± 5.22 | 3.95 ± 1.55 | 5.42 ± | 5.87 ± 2.07 2.26 |
| Tmax (hrs) | 2.45 ± 0.86 | 15.05 ± 9.51 | 5.85 ± 1.92 | 6.90 ± 3.18 |
| AUC(0,72) (hr-ng/ml) | 101.11 ± 41.93 | 136.10 ± 34.58 | 109.37 ± 43.06 | 111.33 ± 36.21 |

In comparing Example 1 (fast) to MS Contin® (fast), there was a statistically significant difference in $C_{max}$. There were no statistically significant differences between the two treatments in $T_{max}$, AUC (0,72), AUC (O, oo) and $T_{1/2}$ (elim) or $T_{1/2}$ (abs). The 90% confidence intervals for all pharmacokinetic parameters were outside the 80–120% limits.

In comparing Example 1 (fed) to MS Contin® (fast), there was a statistically significant difference in $C_{max}$. There were no statistically significant differences between the two treatments in $T_{max}$, AUC (0,72), AUC (O, oo) and $T_{1/2}$ (elim) or $T_{1/2}$ (abs). The 90% confidence intervals for all pharmacokinetic parameters were outside the 80–120% limits.

In comparing Example 1 under fed and fasting conditions, there were no statistically significant differences in $C_{max}$, $T_{max}$, AUD (0,72), AUC (O, oo) and $T_{1/2}$ (elim) or $T_{1/2}$ (abs). The 90% confidence intervals for all pharmacokinetic parameters were outside the 80–120% limits.

The effect of food on the absorption of Example 1 is characterized by a greater $C_{max}$ and extended $T_{max}$ and $T_{1/2}$ (abs) values. The extent of absorption (based on AUCs), however, is less than 3% different under fed and fasted conditions.

In comparing Example 2 (fast) to MS Contin® (fast), there were statistically significant differences in $C_{max}$, $T_{max}$, AUC (0,72), AUC (O, oo) and T½ (elim). There was no statistically significant difference between the two treatments in T½ (abs). The 90% confidence intervals for all pharmacokinetic parameters were outside the 80–120% limits.

Based on the 90% confidence interval analysis, neither Example 1 under fasted or fed conditions nor Example 2 beads are equivalent to MS Contin® tablets. However, while neither of the experimental controlled-release morphine formulations are bioequivalent to MS Contin® tablets, both provide a relatively lower $C_{max}$ and extended $T_{max}$ and apparent $T_{1/2}$ (elim) values.

Linear regression of each pharmacodynamic parameter on the log-transformed concentrations for each subject and treatment resulted in 48 of 240 regressions (48/240; 20%) having an $R^2$ value of 20% or higher, of which 8 (8/240; 3%) had a value of 50% or higher. When analyzed by treatment only, all $R^2$ values were lower than 10%. These values indicate no significant linear relationship between the pharmacodynamic measurements and the log concentrations.

Figure 5:
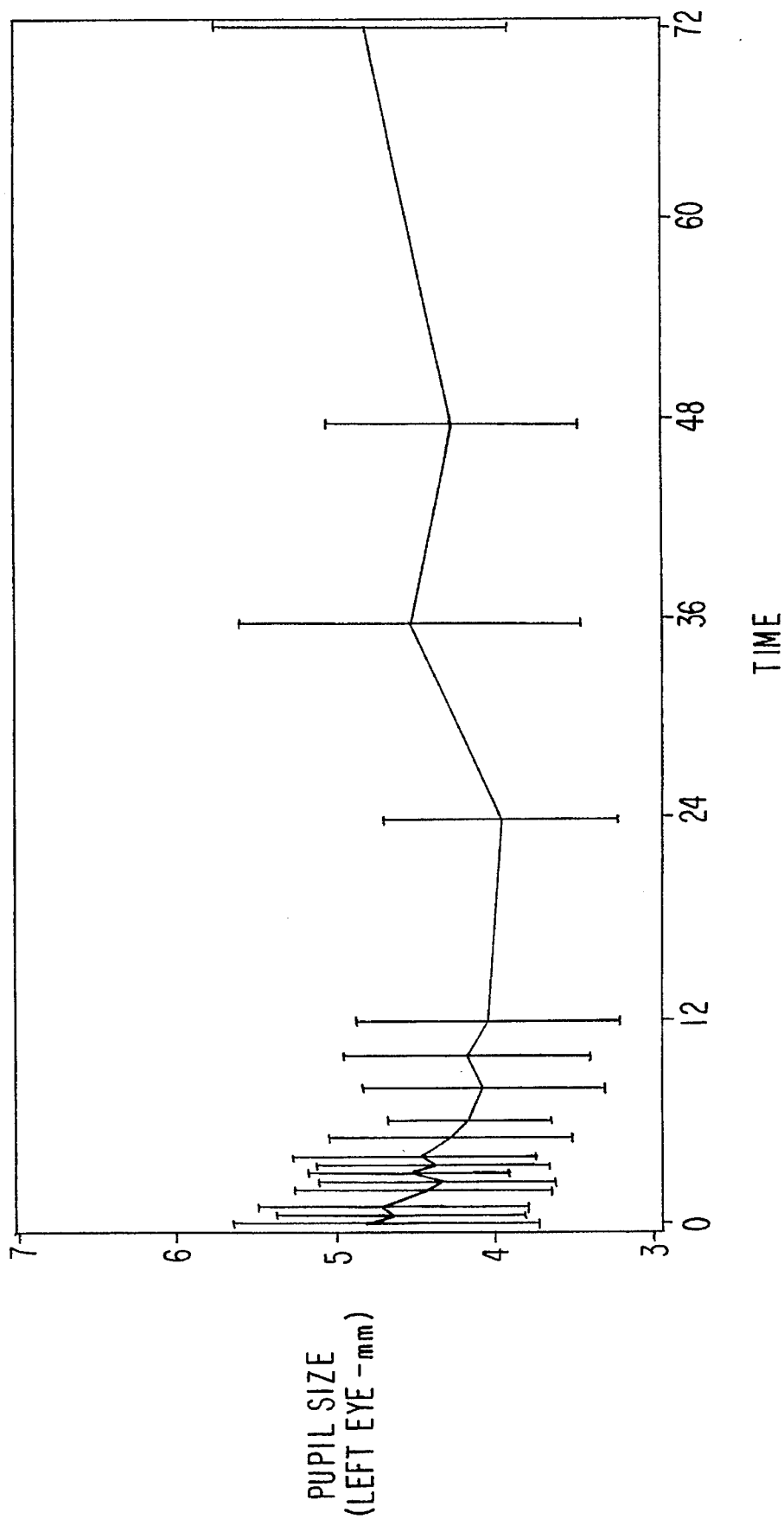
FIG. 5 is a graphical representation of the mean pupil size v. time curve for Example 1 (fasted)
Figure 6:
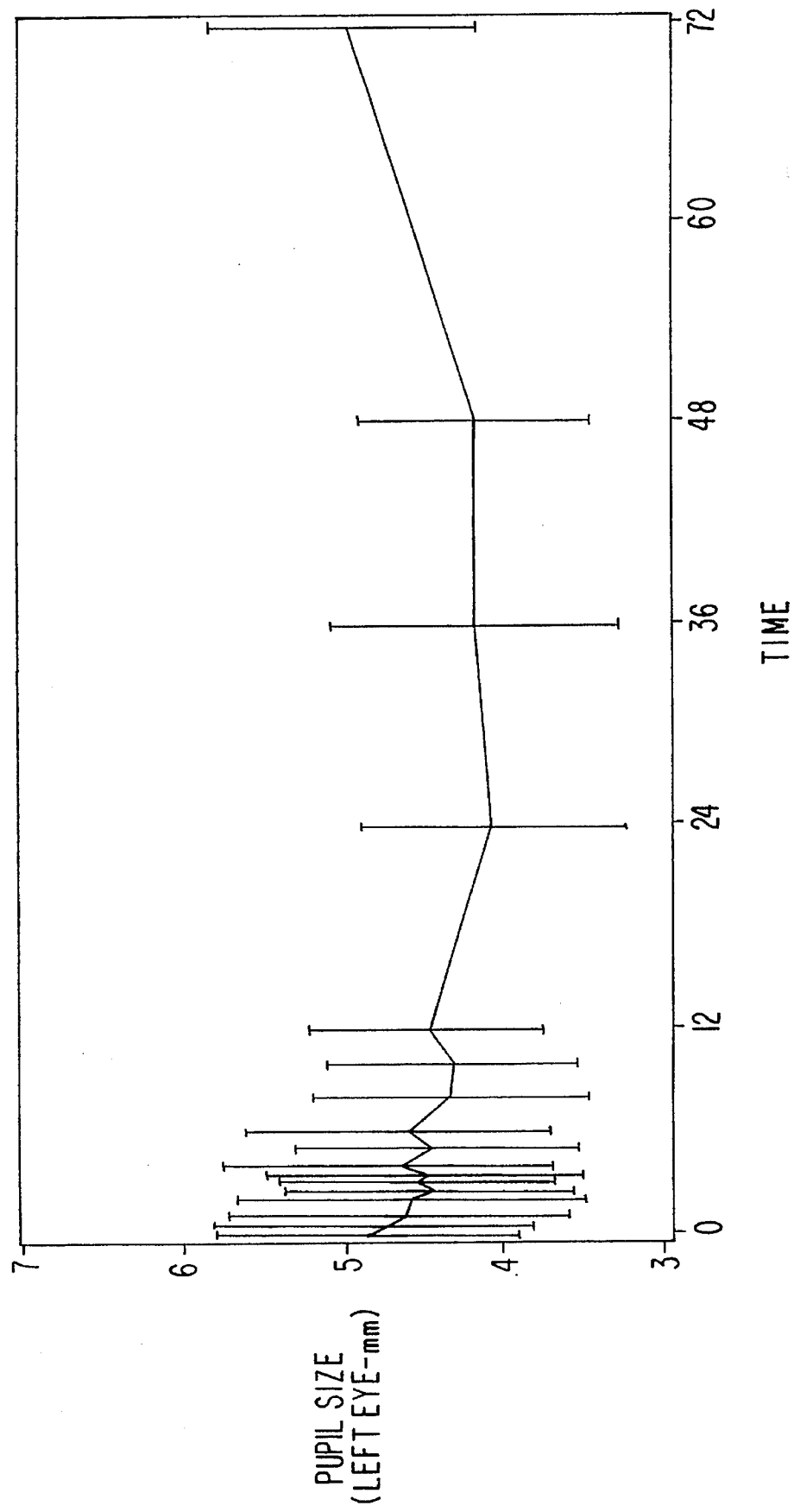
FIG. 6 is a graphical representation of the mean pupil size vs. time curve for Example 2 (fasted)

Examination of the mean hysteresis curves revealed a possible relationship between pupil size and morphine concentration. For MS Contin® and Example 1, pupil size tended to decrease with an increase in morphine concentration, then increase as morphine concentration decreased. FIG. 5 is a graphical representation of the mean pupil size v. time curve for Example 1 (fasted). FIG. 6 is a graphical representation of the mean pupil size vs. time curve for Example 2 (fasted). No relationship was observed between morphine concentrations and any of the other parameters.

Two subjects (20%) reported six adverse experiences while receiving MS Contin®. Three subjects (30%) reported six adverse experiences while receiving controlled-release morphine beads (Example 1; fasted). One subject in each of the following treatment groups reported a single adverse experience: Example 1 (fed) and Example 2 (fasted). No clinically significant changes in physical examination or EKG results, clinical laboratory values or vital sign measurements occurred during the study.

Modified Specific Drug Effect Questionnaire

The questionnaire was a modification of the 22-item questionnaire used by Jasinski, D. R. (1977) Assessment of the Abuse Potential of Morphine-Like Drugs (Methods Used in Man). In *Drug Addiction I* (Martin, W. R., ed.) pp. 197–258. Springer-Verlag, New York; and Preston, K. L., Jasinski, D. R., and Testa, M. (1991) Abuse Potential and Pharmacological Comparison of Tramadol and Morphine. *Drug and Alcohol Dependence* 27:7–17. The questionnaire consisted of 10 items to be rated by the subject and observer. The items were related to signs of opiate-agonist drugs and were as follows:

Subject's Questions

1. Do you feel any effects of the drugs?
2. Is your skin itchy?
3. Are you relaxed?
4. Are you sleepy?
5. Are you drunk?
6. Are you nervous?
7. Are you full of energy?

8. Do you need to talk?

9. Are you sick to your stomach?

10. Are you dizzy?

The subject rated each of these questions by placing a vertical mark along a 100-mm VAS anchored at one end by "not at all" and at the other end by "an awful lot".

Observer's Questions

1. Is the subject showing any drug effect?
2. Is the subject scratching?
3. Is the subject relaxed?
4. Is the subject drunk?
5. Is the subject nervous?
6. Is the subject talking?
7. Is the subject vomiting?
8. Is the subject confused?
9. Is the subject restless?
10. Is the subject perspiring?

Figure 7:
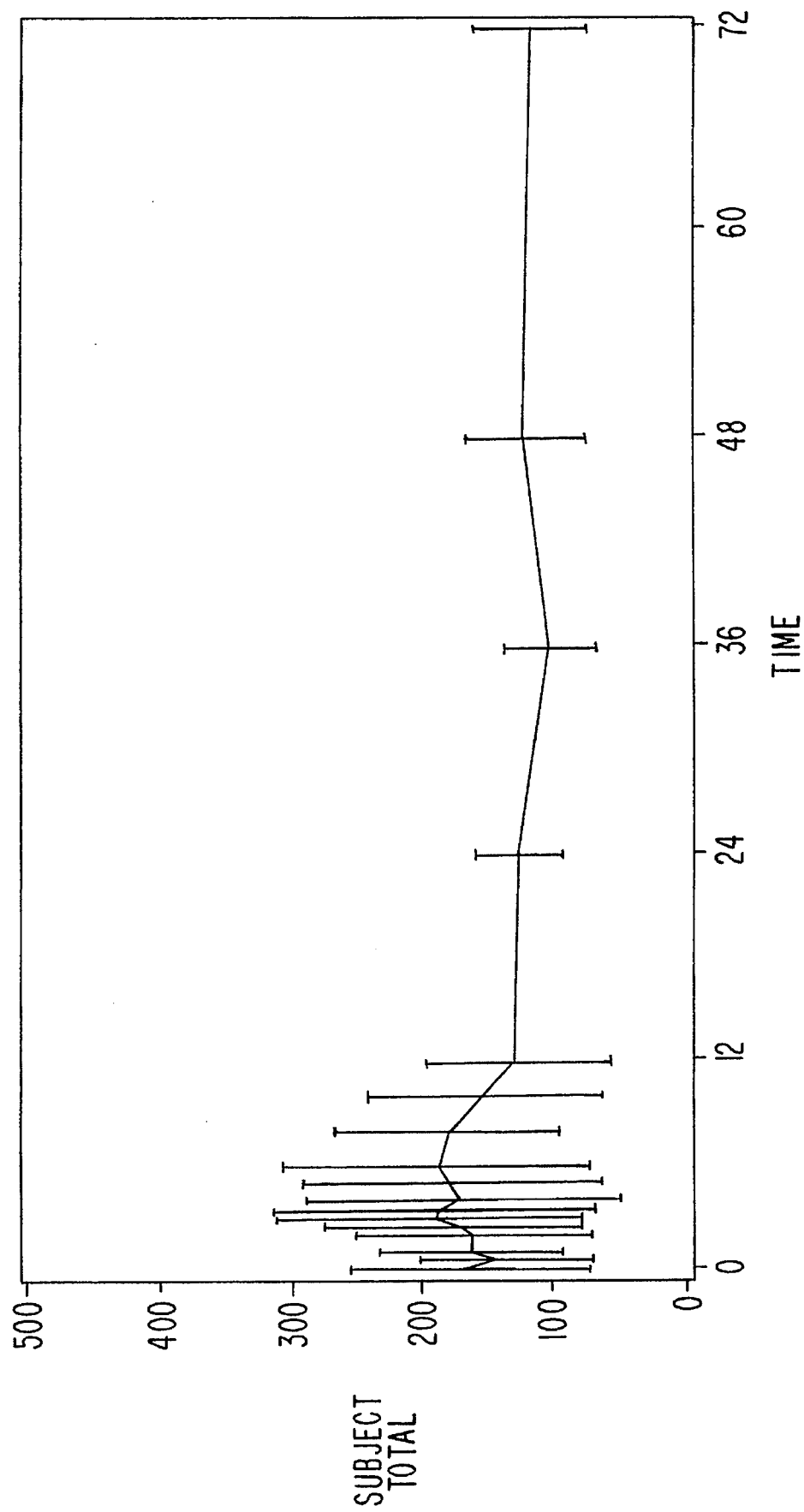
FIG. 7 is a graphical representation of the means subject questionnaire vs. time curve for Example 1 (fasted)
Figure 8:
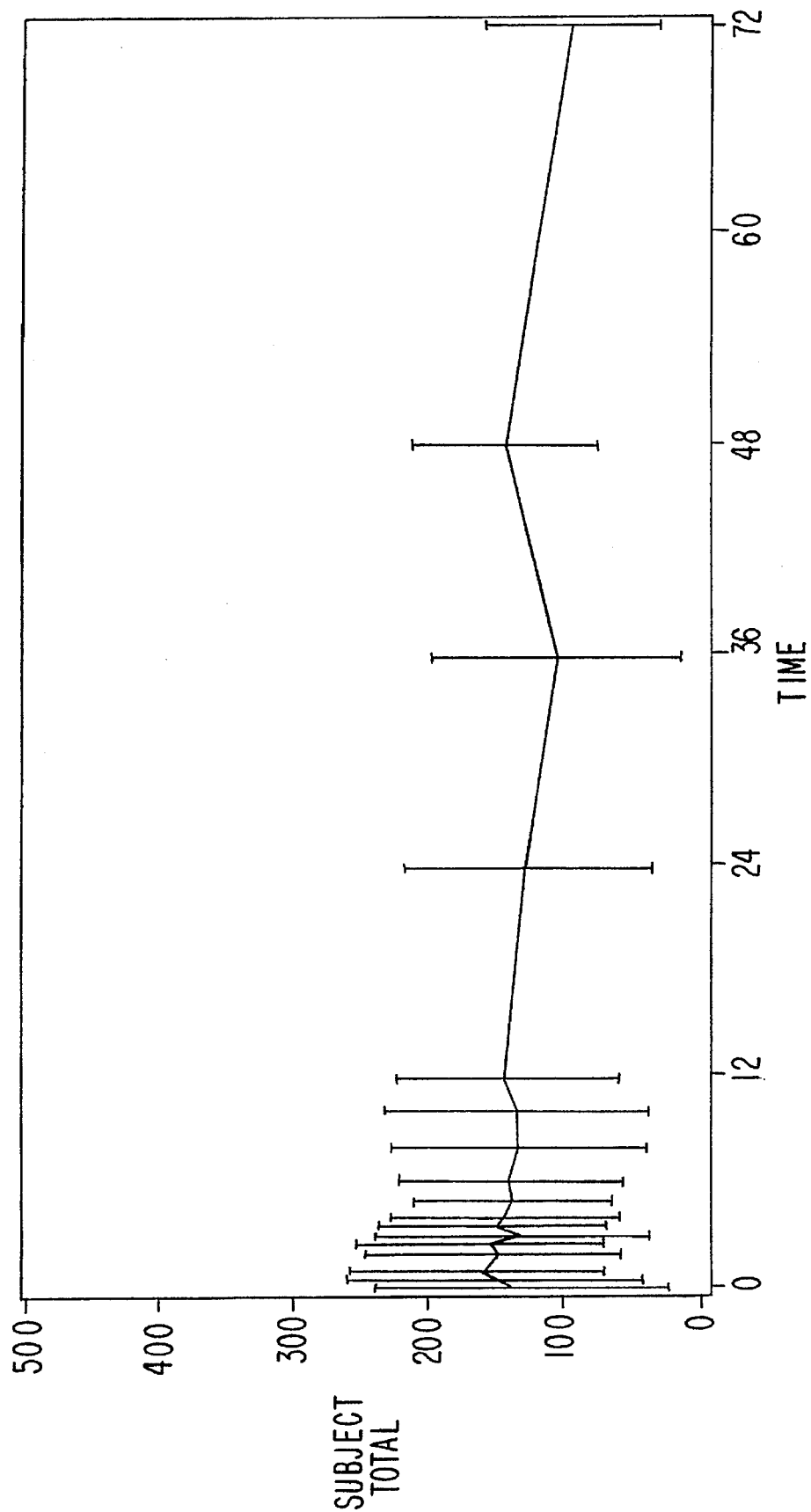
FIG. 8 is a graphical representation of the means subject questionnaire vs. time curve for Example 2 (fasted)

The observer rated each of these questions by placing a vertical mark along a 100-mm VAS anchored at one end by "not at all" and at the other end by "extremely". FIG. 7 is a graphical representation of the means subject questionnaire vs. time curve for Example 1 (fasted). FIG. 8 is a graphical representation of the means subject questionnaire vs. time curve for Example 2 (fasted).

Adverse Experiences

Adverse experiences, whether spontaneously reported or elicited upon direct questioning, were recorded and evaluated promptly by the principal investigator to determine the severity, duration and initiation of corrective measures, if warranted. Subjects were to be followed until they returned to baseline status.

Analytical

Plasma morphine analyses were conducted using high performance liquid chromatography (HPLC). The limit of quantification was 0.5 ng/mL. Appendix V contains the plasma morphine analytical report.

Statistical and Pharmacometric Methods

Parameters

The serial plasma morphine values, collected from each subject and treatment, were corrected for the zero-hour value by subtraction of the zero-hour value from all subsequent values in that series.

Any serial dataset in which the zero-hour value exceeded the minimum assay sensitivity was, as noted above, deemed inadmissible for data analysis. The following parameters were estimated for each subject and treatment, using the baseline-corrected plasma levels.

$C_{max}$ (ng/ml)—largest observed plasma morphine value $T_{max}$ (hours)—time of occurrence of $C_{max}$, relative to time of dosing $T_{1/2}$ (elim; hours)—apparent half-life of plasma morphine elimination calculated according to:

$$T_{1/2} (elim) - 0.693/K_e$$

where $K_e$ is the terminal first-order apparent elimination rate constant calculated by PROC NLIN in SAS Release 6.07 (SAS Institute, Cary, N.C.).

$T_{1/2}$ (abs; hrs)—apparent half-life of absorption calculated according to:

$$T_{1/2} (abs) - 0.693/K_e$$

Figure 9:
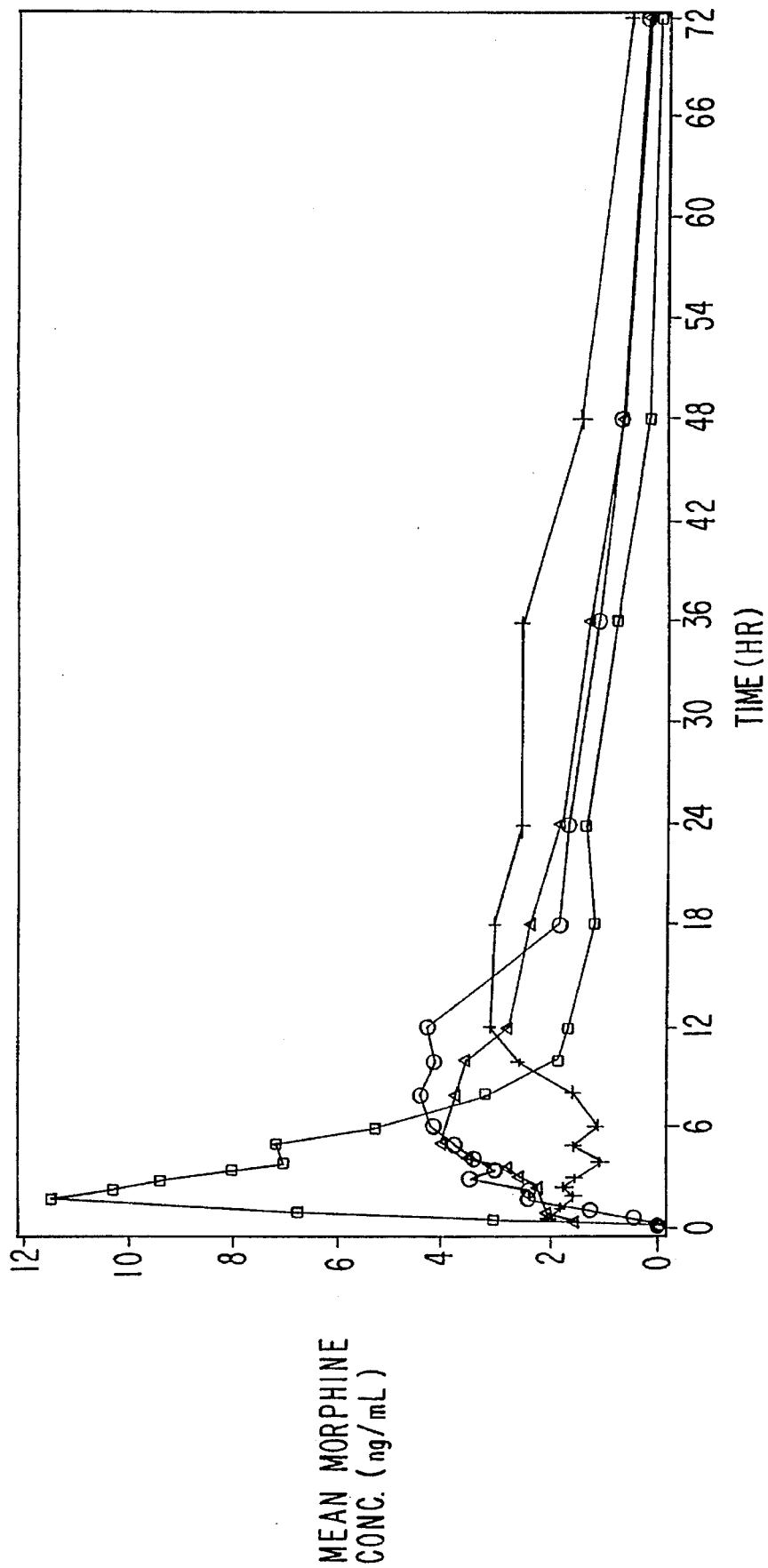
FIG. 9 is a graphical representation of the mean plasma morphine concentration-time profile obtained with the Comparative Example (MS Contin 30 mg)(fasted) as compared to the capsules of Example 1 (fed and fasted) and Example 2 (fasted)

FIG. 9 is a graphical representation of the mean plasma morphine concentration-time profile obtained with the Comparative Example (MS Contin 30 mg)(fasted) as compared to the capsules of Example 1 (fed and fasted) and Example 2 (fasted).

From the results set forth above, it can be seen that the formulation of Example 1 attains a higher and earlier Cmax but a slightly lower extent of morphine absorption than the formulation of Example 2. Visual examination of the time-action data in respect to sedation, respiratory rate, pupil size, and combined scores from a questionnaire of opioid effects reported by the subjects at serial times following each treatment reveals greater degree of intensity of each pharmacodynamic endpoint during the earlier (e.g., 4–8 hours) portion of the time-action curves.

EXAMPLE 3

Beads with a higher loading of morphine sulfate were produced with the use of the powder layering technique in the Glatt Rotor Processor. The formulation of the high load beads is set forth in Table 4 below:

TABLE 4

| Ingredient | High Load Bead mg/unit | Percent (%) |
|---|---|---|
| Morphine Sulfate Powder | 30.0 mg | 63.3% |
| Lactose | 6.0 mg | 12.7% |
| Povidone C-30 | 1.25 mg | 2.6% |
| Sugar Beads | 7.75 mg | 16.4% |
| Opadry | 2.37 mg | 5.0% |
| Purified Water | qs | — |
| Total | 47.37 mg | 100.0% |

The sustained-release coating comprised an acrylic polymer (i.e., Eudragit® RL). A HPMC protective coat was also included between the Eudragit layer and the morphine immediate release layer to further enhance stability. The formula of the sustained-release coating of Example 3 is set forth in Table 5 below:

TABLE 5

| Ingredient | Amt/Unit (mg) | Percent (%) |
|---|---|---|
| Morphine (high load) base beads | 42.63 mg | 78.8% |
| Retardant Coating | | |
| Eudragit RS 30D | 2.1 mg | 3.9% |
| Eudragit RL 30D | 0.05 mg | 0.1% |
| Triethyl Citrate | 0.45 mg | 0.8% |
| Talc | 0.85 mg | 1.6% |
| Overcoatings | | |
| Opadry Blue YS-1-10542A | 2.45 mg | 4.5% |
| Purified Water | qs | — |
| Morphine Sulfate Powder | 3.0 mg | 5.5% |
| Opadry Blue YS-1-10542A | 2.55 mg | 4.8% |
| Purified Water | qs | — |
| Total | 54.08 mg | 100.0% |

The sustained-release and the immediate release coatings were applied as follows. The Eudragit RL 30D was plasticized with triethyl citrate and talc for approximately 30 minutes. A load of the morphine sulfate beads was charged into a Wurster Insert of a Glatt equipped with a 1.2 mm spray nozzle and the beads are coated to a weight gain of 5%. The final protective Opadry dispersion overcoat was then applied in the Wurster Insert. Upon completion the beads were cured for two days in a dry oven of 45° C. The cured beads were then filled into gelatin capsules at a 30 mg strength. The cured beads were then filled into gelatin capsules at a strength of 30 mg.

The capsules were then subjected to dissolution testing. Dissolution testing was conducted on the finished products via USP Apparatus II-(Paddle Method). The capsules were placed into 700 ml of simulated gastric fluid (without enzymes) for the first hour at 100 rpm and 37° C., and then placed into 900 ml of simulated gastric fluid (without enzymes) after the first hour. The results of dissolution testing is set forth in Table 6 below:

TABLE 6

| Time | Percent Morphine Sulfate Dissolved |
|---|---|
| 1 hour | 11.7% |
| 2 hours | 12.1% |
| 4 hours | 22.0% |
| 8 hours | 45.3% |
| 12 hours | 63.7% |
| 18 hours | 81.8% |
| 24 hours | 92.5% |

Clinical Evaluation of Example 3

Thirteen normal, healthy male subjects were enrolled in this five-way crossover, randomized, open-label study assessing the effect of food on the pharmacokinetics and pharmacodynamics of single 30-mg doses (capsules) of Example 3. The pharmacokinetic and pharmacodynamic results of the extended-release formulations in these fed and fasted subjects were also compared with those of MS Contin® 30 mg tablets in fasted subjects. Plasma morphine level was used to calculate pharmacokinetic parameters including: (a) apparent absorption and elimination rates; (b) area-under-the-curve (AUC); (c) maximum plasma concentration ($C_{max}$); (d) time to maximum plasma concentration ($T_{max}$); (e) $T_{1/2}$ (abs), and (f) $T_{1/2}$ (elim). Pharmacodynamic effects were assessed based on evaluations of mood, sedation, respiratory rate, pupillometry, and subject's adjective questionnaire.

Plasma morphine concentrations were determined by a high-performance liquid chromatographic procedure. All subjects completed the study and were included in the biopharmaceutical analysis. Arithmetic mean $C_{max}$, $T_{max}$, AUC, half-lives calculated from individual plasma morphine concentration-versus-time, and oral bioavailability data are set forth in Tables 7A and 7B below:

TABLE 7A

| Pharmaco-kinetic Parameter | Ex. 3 (Fed) | Ex. 3 (Fast) | MS Contin® (Fasted) |
|---|---|---|---|
| $C_{max}$ (ng/ml) | 5.45 | 4.03 | 11.65 |
| $T_{max}$ (hours) | 8.04 | 12.92 | 2.77 |
| AUC (0.72) | 118.12 | 140.79 | 114.05 |

TABLE 7A-continued

| Pharmaco-kinetic Parameter | Ex. 3 (Fed) | Ex. 3 (Fast) | MS Contin® (Fasted) |
|---|---|---|---|
| (hr-ng/ml) | | | |
| AUC (0,00) | 137.67 | 166.19 | 114.05 |
| (hr-ng/ml) | | | |
| $T_{1/2}$(elim; hrs) | 21.19 | 54.51 | 1.26 |
| $T_{1/2}$(abs; hrs) | 3.12 | 2.44 | 3.34 |

TABLE 7B

| Pharmaco-kinetic Parameter | $F_0$ (%) 90% C.I. (Ex 3: Fed vs. Fast) | Ex. 3 vs. MS Contin® (Both Fasted) |
|---|---|---|
| $C_{max}$ (ng/ml) | 164.36 (113.1–215.6) | 29.54 (14.3–44.7) |
| $T_{max}$ (hours) | 53.49 (13.3–93.7) | 514.28 (306.8–721.7) |
| AUC (0.72) (hr-ng/ml) | 89.93 (64.8–115.1) | 119.35 (89.2–149.5) |
| AUC (0,00) (hr-ng/ml) | 86.56 (62.5–110.6) | 143.48 (108.6–178.1) |
| $T_{1/2}$(elim; hrs) | 34.53 (7.4–61.7) | 1609.0 (1170–2048) |
| $T_{1/2}$(abs; hrs) | 135.27 (83.5–187.0) | 191.45 (92.0–290.9) |

$F_0$ (%) = Oral bioavailability (Test mean/Reference mean)

Table 8 provides the mean (± S.D.) plasma morphine concentrations (ng/ml) following dosing with MS Contin® and Example 3.

TABLE 8

Mean Plasma Morphine Concentrations ± Standard Deviation Following Administration

| Time (hours) | Ex. 3 30 mg Fed | Ex. 3 30 mg Fasted | MS Contin® 30 mg Fasted |
|---|---|---|---|
| 0.00 | 0.00 ± 0.00 | 0.00 ± 0.00 | 0.00 ± 0.00 |
| 0.50 | 0.201 ± 0.447 | 2.00 ± 1.48 | 3.42 ± 1.82 |
| 1.00 | 0.331 ± 0.479 | 2.27 ± 0.799 | 6.09 ± 2.03 |
| 2.00 | 1.65 ± 1.53 | 2.19 ± 0.936 | 8.82 ± 2.61 |
| 2.50 | 3.06 ± 1.04 | 2.20 ± 0.798 | 9.12 ± 2.97 |
| 3.00 | 3.53 ± 1.82 | 2.24 ± 1.05 | 9.91 ± 5.32 |
| 3.50 | 3.06 ± 1.16 | 2.87 ± 1.94 | 8.83 ± 3.58 |
| 4.00 | 3.23 ± 1.04 | 2.33 ± 1.13 | 8.12 ± 3.26 |
| 5.00 | 4.01 ± 1.50 | 2.91 ± 0.933 | 7.79 ± 3.47 |
| 6.00 | 4.00 ± 2.09 | 2.96 ± 1.24 | 6.07 ± 3.69 |
| 8.00 | 4.03 ± 1.90 | 2.58 ± 1.24 | 4.68 ± 3.88 |
| 10.0 | 3.95 ± 1.89 | 1.95 ± 0.965 | 2.61 ± 1.43 |
| 12.0 | 3.20 ± 1.47 | 2.18 ± 0.983 | 1.58 ± 0.815 |
| 18.0 | 2.06 ± 1.02 | 2.75 ± 1.53 | 1.46 ± 0.745 |
| 24.0 | 2.10 ± 0.963 | 2.72 ± 0.971 | 1.34 ± 0.890 |
| 36.0 | 1.66 ± 1.05 | 2.65 ± 1.18 | 1.08 ± 0.971 |
| 48.0 | 0.872 ± 0.681 | 1.53 ± 0.851 | 0.528 ± 0.831 |
| 72.0 | 0.300 ± 0.529 | 0.468 ± 0.650 | 0.00 ± 0.00 |

Table 9 provides the mean (± S.D.) pharmacokinetic parameters following dosing with MS Contin® And Example 3.

TABLE 9

Mean Pharmacokinetic Parameters ± Standard Deviation Following Administration of Each Formulation

| Parameter | Ex. 3 30 mg Fed | Ex. 3 30 mg Fasted | Ms Contin® 30 mg Fasted |
|---|---|---|---|
| $C_{max}$ | 5.45 ± 1.68 | 4.03 ± 1.55 | 11.65 ± 4.82 |

TABLE 9-continued

Mean Pharmacokinetic Parameters ± Standard Deviation Following Administration of Each Formulation

| Parameter | Ex. 3 30 mg Fed | Ex. 3 30 mg Fasted | Ms Contin ® 30 mg Fasted |
|---|---|---|---|
| (ng/ml) | | | |
| Tmax (hrs) | 8.04 ± 8.31 | 12.92 ± 14.66 | 2.77 ± 0.927 |
| AUC(0,72) (hr-ng/ml) | 118.12 ± 36.77 | 140.79 ± 51.23 | 114.05 ± 42.42 |

The ratios of least-squares mean AUC for the 30 mg capsules of Example 3 given under fed and fasted conditions indicate that AUC values under fed conditions are within ±20% of those under fasted conditions. The value of $C_{max}$ was 64% greater under fed conditions. The value of $T_{max}$ under fed conditions was approximately 50% of that when given under fasted conditions. The apparent absorption rate was approximately 35% greater under fed conditions, and the apparent elimination rate under fed conditions was approximately 35% of that under fasted conditions, indicating that absorption of morphine is slowed by the presence of food, and elimination rate is increased.

The ratios of least-squares mean AUC for the 30 mg capsule of Example 3 and the MS Contin® 30 mg tablet indicate that AUC (0,72) values for Example 3 are within ±20% of those for MS Contin®, and AUC (0,00) values are 44% greater for Example 3. The value of $C_{max}$ for Example 3 was 29.5% of that for MS Contin®. The value of $T_{max}$ under fed conditions was over five times that for Example 3. The apparent absorption rate was approximately 91% greater for Example 3, and the apparent elimination rate for Example 3 was over 16 times that for MS Contin®, indicating that absorption and elimination of morphine is slower for Example 3.

Linear regression of each pharmacodynamic parameter on the log-transformed concentrations for each subject and treatment resulted in 74 of 315 regressions (24%) having an $R^2$ value of 20% or higher, and 12 of 315 (4%) having a value of 50% or higher. When analyzed by treatment only, there were zero $R^2$ values higher than 10%. Of those individual $R^2$ values above 20%, 21 occurred in the 63 regressions (33%) of Subject's Modified Specific Drug Effect Questionnaire scores on log concentration, and 7 of the 63 (11%) were above 50%. These values indicate a possible linear relationship between the log concentrations and Subject's MSDEQ scores. Examination of the mean hysteresis curves also reveals a possible relationship between morphine concentration and Subject's MSDEQ scores. For each formulation, Subject Modified Specific Drug Effect Questionnaire scores tended to increase with an increase in morphine concentration, then decrease as morphine concentration decreased. No relationships were observed between morphine concentrations and any of the other pharmacodynamic parameters.

Figure 10:
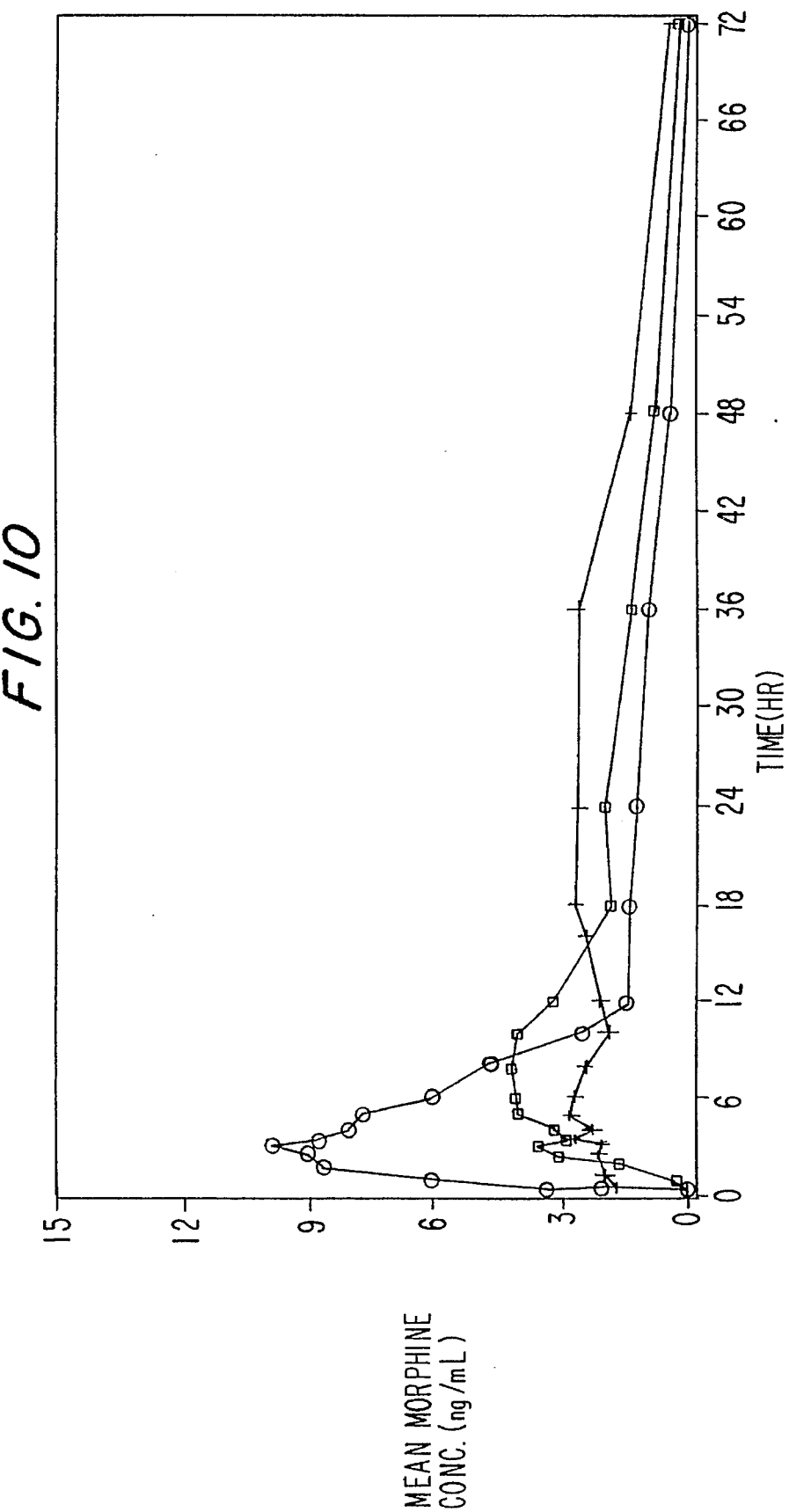
FIG. 10 is a graphical representation of the mean plasma morphine concentration-time profile obtained with the Comparative Example (MS Contin 30 mg)(fasted) as compared to the capsules of Example 3 (fed and fasted)
Figure 11:
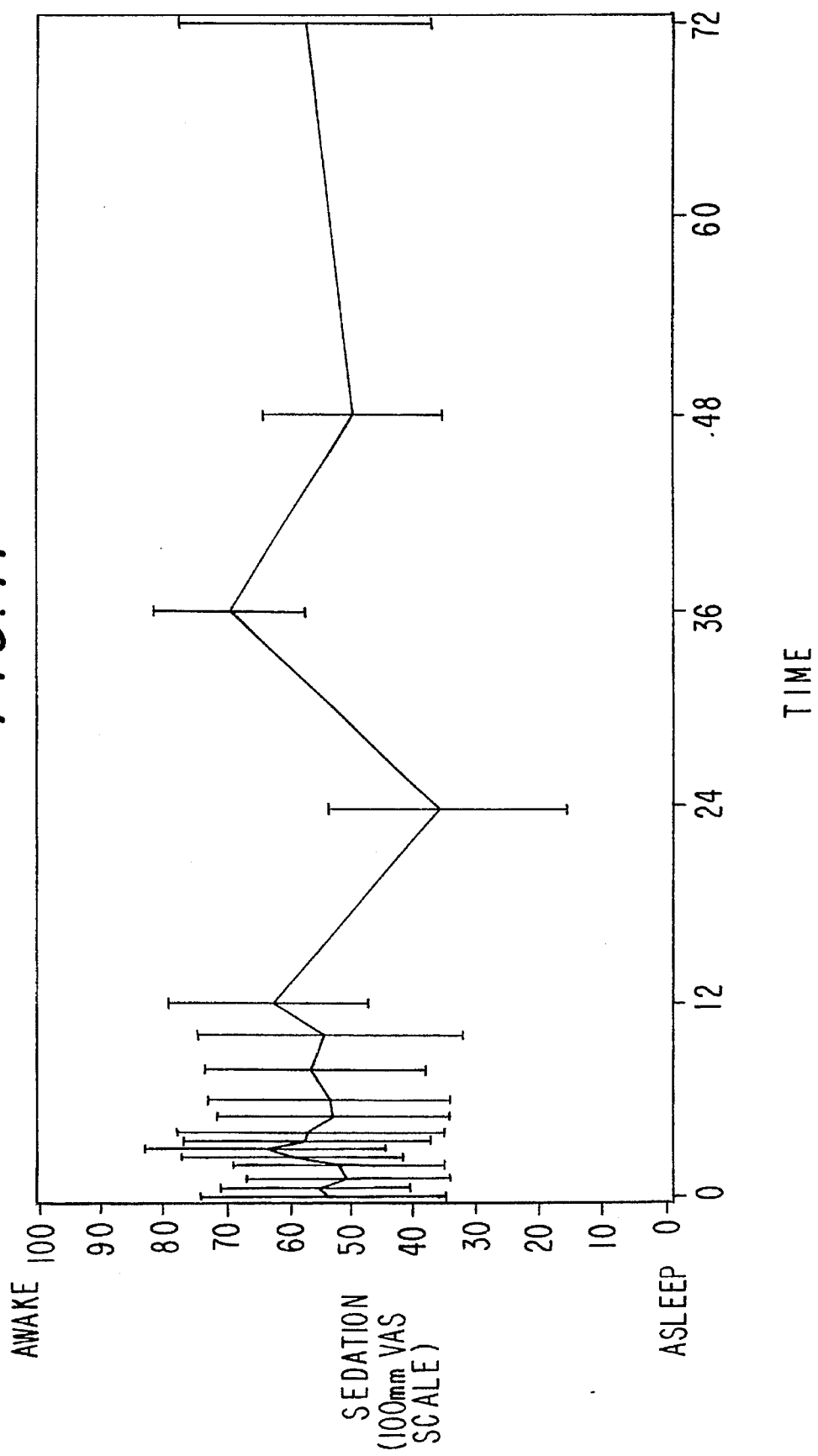
FIG. 11 is a graphical representation of the mean sedation vs. time curve for Example 3 (fasted)
Figure 12:
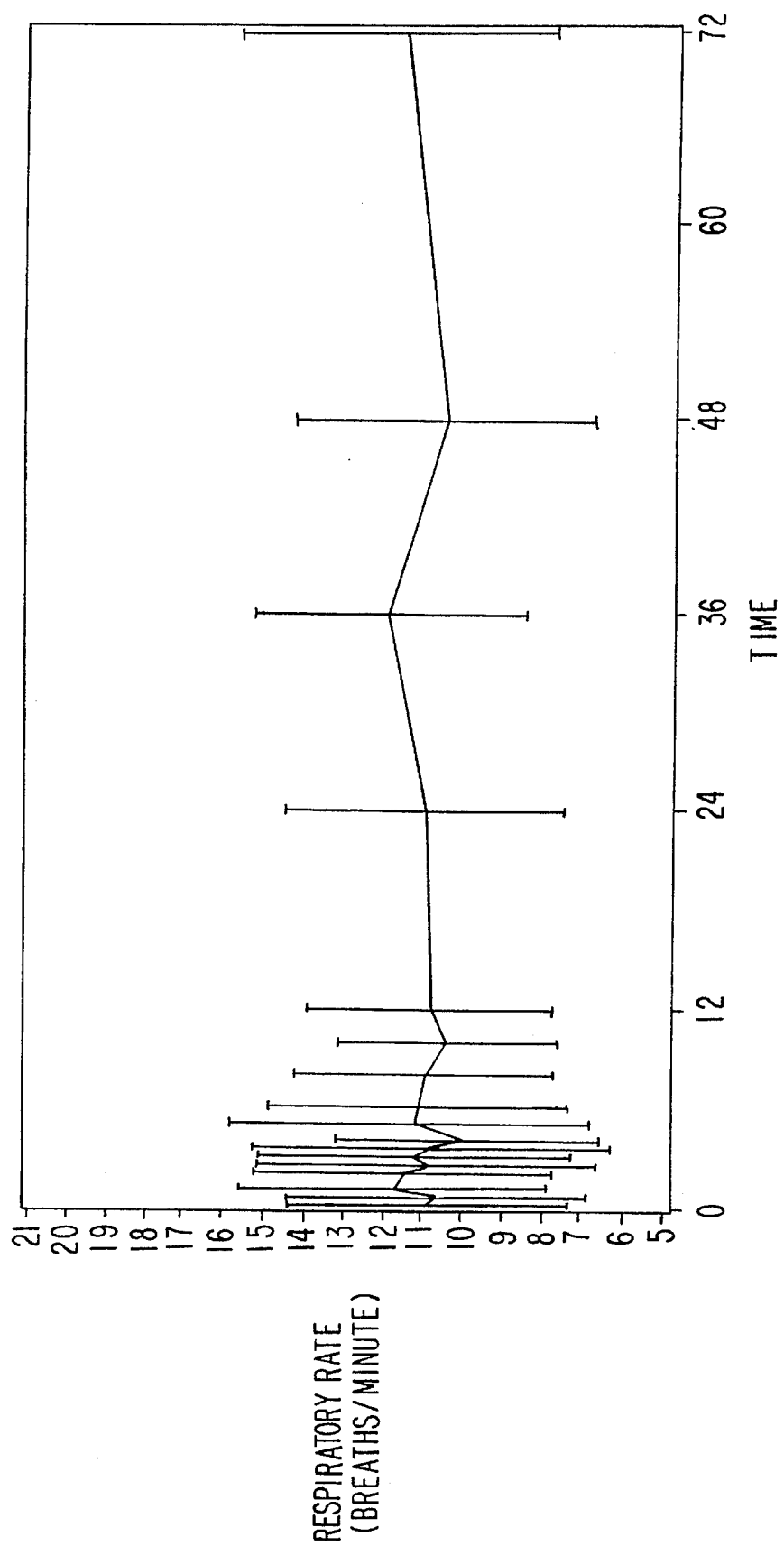
FIG. 12 is a graphical representation of the mean respiratory rate vs. time curve for Example 3 (fasted)
Figure 13:
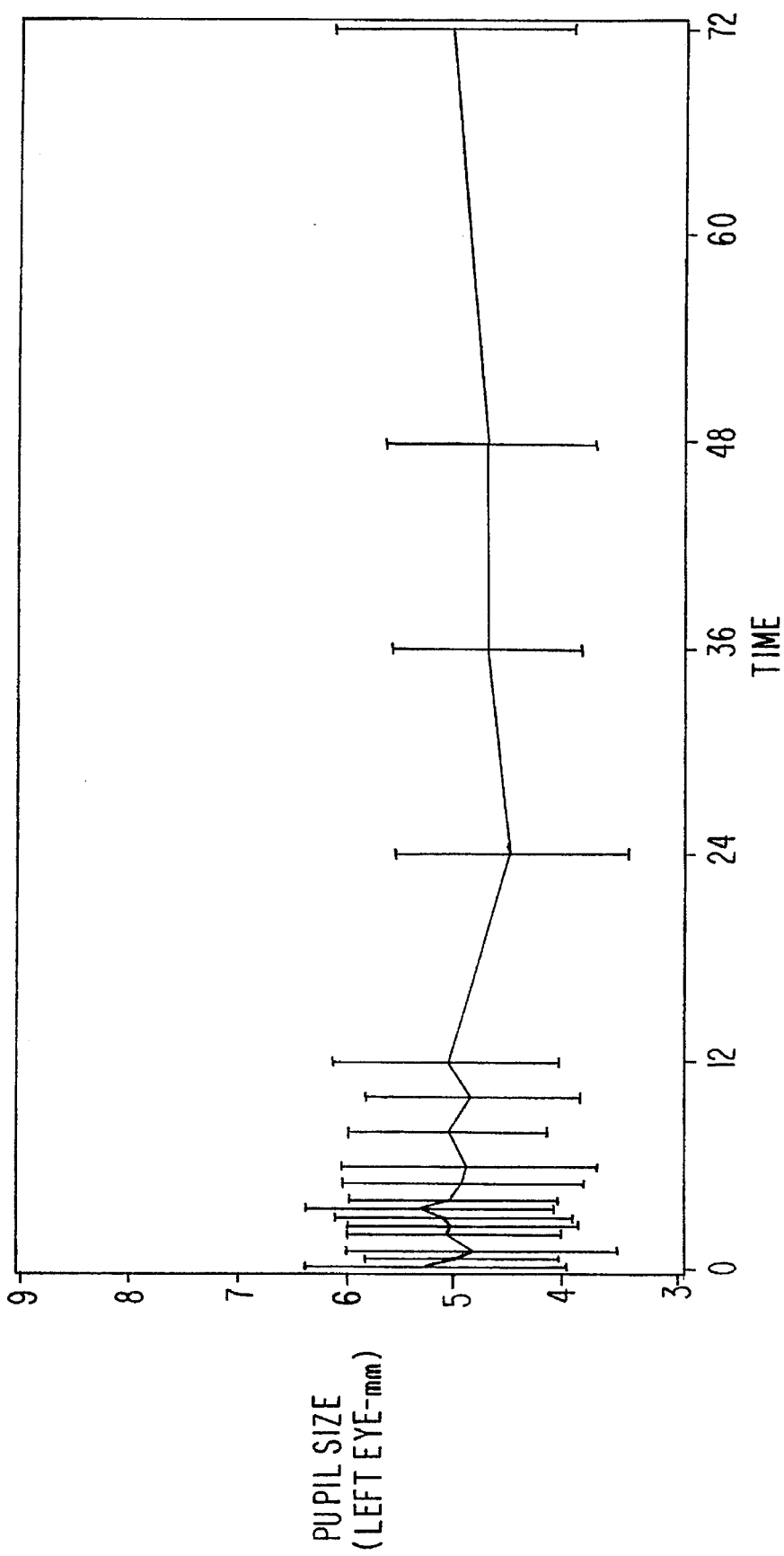
FIG. 13 is a graphical representation of the mean pupil size v. time curve for Example 3 (fasted)
Figure 14:
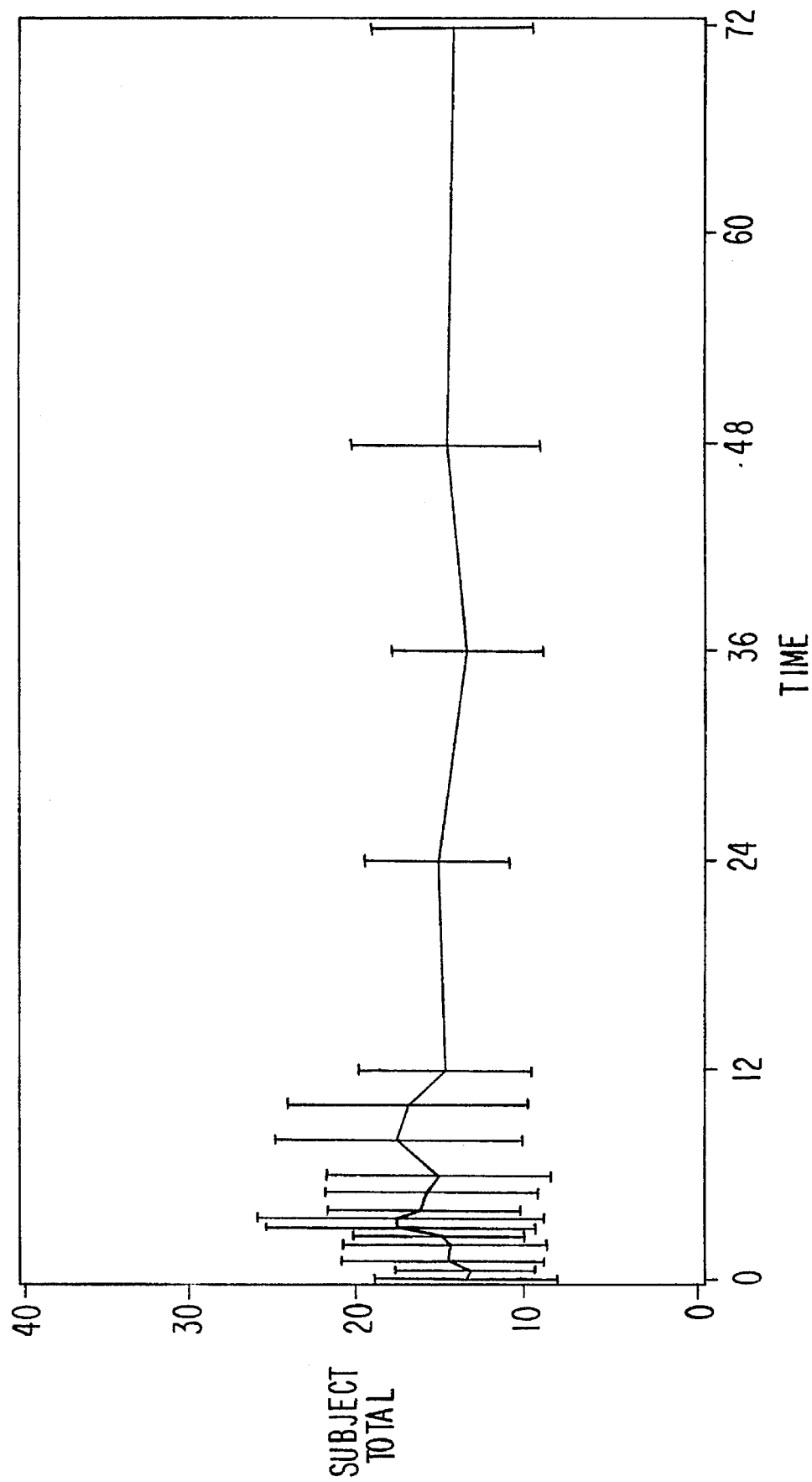
FIG. 14 is a graphical representation of the mean subject modified specific drug effect questionnaire vs. time curve for Example 2 (fasted).

FIG. 10 is a graphical representation of the mean plasma morphine concentration-time profile obtained with the Comparative Example (MS Contin 30 mg)(fasted) as compared to the capsules of Example 3 (fed and fasted). FIG. 11 is a graphical representation of the mean sedation vs. time curve for Example 3 (fasted). FIG. 12 is a graphical representation of the mean respiratory rate vs. time curve for Example 3 (fasted). FIG. 13 is a graphical representation of the mean pupil size v. time curve for Example 3 (fasted). FIG. 14 is a graphical representation of the mean subject modified specific drug effect questionnaire vs. time curve for Example 2 (fasted).

The examples provided above are not meant to be exclusive. Many other variations of the present invention would be obvious to those skilled in the art, and are contemplated to be within the scope of the appended claims.

What is claimed is:

1. A method for providing effective pain management in humans for a time period of about 24 hours, comprising preparing a solid, controlled-release oral dosage form by incorporating an analgesically effective amount of an opioid analgesic into a controlled release dosage form which provides a rapid rate of initial rise of the plasma concentration of said opioid such that the peak plasma level of said opioid analgesic obtained in-vivo occurs from about 2 to about 8 hours after administration of the dosage form, and which provides large peak to trough fluctuations in opioid levels even after repeated dosing, such that said dosage form provides effective pain relief for at least about 24 hours when administered to a human patient.

2. The method of claim 1, wherein said opioid analgesic is selected from the group consisting of hydromorphone, oxycodone, dihydrocodeine, codeine, dihydromorphine, morphine, buprenorphine, salts of any of the foregoing, and mixtures of any of the foregoing.

3. The method of claim 1, wherein said opioid is morphine and the maximum plasma concentration of said opioid is from about 2 ng/ml to about 14 ng/ml.

4. The method of claim 1, wherein said opioid is morphine and the maximum plasma concentration of said opioid is from about 3 ng/ml to about 8 ng/ml.

5. The method of claim 1, further comprising providing a formulation having an extended $T_{max}$.

6. The method of claim 1, further comprising providing a formulation having an extended $T_{max}$ for about 2 to about 4 hours.

7. The method of claim 1, further comprising including an portion of the dose of said opioid in immediate release form, said portion of said dose of said opioid being sufficient to provide loading dose of said opioid causing a significantly shortened and a large peak to trough fluctuation in said concentration of said opioid during said 24-hour efficacy period.

8. The method of claim 1, further comprising providing said opioid formulation such that it exhibits first order release characteristics.

9. The method of claim 1, further comprising preparing said dosage form such that at least about 10.2% of said opioid analgesic is released after 1 hour when measured according to the USP Paddle Method utilizing a USP Apparatus Type II in 700 ml of simulated gastric fluid.

10. The method for providing effective pain management in humans, comprising preparing a solid, controlled release oral dosage form by incorporating an analgesically effective amount of an opioid analgesic into a controlled release dosage form which provides a dissolution profile in acidic pH such that at least about 10.2% of said opioid analgesic is released after 1 hour when measured according to the USP Paddle Method utilizing a USP Apparatus Type II in 700 ml of simulated gastric fluid, wherein said dosage form further provides an in vivo peak plasma level of said opioid analgesic at about 2 to about 8 hours after administration of said dosage form to a patient and said dosage form provides effective pain relief for at least about 24 hours.

* * * * *